(12) United States Patent
Lansonneur et al.

(10) Patent No.: US 11,992,703 B2
(45) Date of Patent: May 28, 2024

(54) CORRELATION OF DOSE AND DOSE RATE INFORMATION TO VOLUME FOR RADIATION TREATMENT PLANNING

(71) Applicants: Varian Medical Systems International AG., Cham (CH); Varian Medical Systems Particle Therapy GmbH & Co. KG, Troisdorf (DE); Varian Medical Systems, Inc., Palo Alto, CA (US)

(72) Inventors: Pierre Lansonneur, Helsinki (FI); Perttu Niemela, Espoo (FI); Viljo Petaja, Espoo (FI); Simon Busold, Cologne (DE); Michiko Rossi, Espoo (FI); Matti Sakari Ropo, Helsinki (FI); Michael Folkerts, Carrollton, TX (US); Jessica Perez, Geneva (CH); Christel Smith, Santa Barbara, CA (US); Adam Harrington, Glastonbury, CT (US); Eric Abel, San Jose, CA (US); Lauri Halko, Helsinki (FI)

(73) Assignees: VARIAN MEDICAL SYSTEMS PARTICLE THERAPY GMBH & CO. KG, Troisdorf (DE); VARIAN MEDICAL SYSTEMS, INC., Palo Alto, CA (US); SIEMENS HEALTHINEERS INTERNATIONAL AG, Steinhausen (CH)

( * ) Notice: Subject to any disclaimer, the term of this patent is extended or adjusted under 35 U.S.C. 154(b) by 273 days.

(21) Appl. No.: 17/323,942

(22) Filed: May 18, 2021

(65) Prior Publication Data
US 2021/0393982 A1 Dec. 23, 2021

Related U.S. Application Data

(60) Provisional application No. 63/043,027, filed on Jun. 23, 2020.

(51) Int. Cl.
*A61N 5/10* (2006.01)

(52) U.S. Cl.
CPC ........ *A61N 5/1031* (2013.01); *A61N 5/1071* (2013.01); *A61N 2005/1074* (2013.01);
(Continued)

(58) Field of Classification Search
None
See application file for complete search history.

(56) References Cited

U.S. PATENT DOCUMENTS

| | | | | |
|---|---|---|---|---|
| 7,831,289 B2 * | 11/2010 | Riker | ............... | G16H 70/20 378/65 |
| 2004/0165696 A1 * | 8/2004 | Lee | ............... | G16H 20/40 378/65 |

(Continued)

FOREIGN PATENT DOCUMENTS

WO 2020181036 9/2020

OTHER PUBLICATIONS

Podesta, Mark et al., "Dose Rate Mapping of VMAT Treatments" Physics in Medicine and Biology, Institute of Physics Publishing, Bristol GB, vol. 61, No. 11, May 10, 2016 (May 10, 2016). pp. 4048-4060.

*Primary Examiner* — Christine H Matthews
*Assistant Examiner* — Marc D. Honrath
(74) *Attorney, Agent, or Firm* — Harness, Dickey & Pierce, P.L.C.

(57) ABSTRACT

A method used for planning radiation treatment accessing information that includes calculated doses and calculated dose rates for sub-volumes in a treatment target, and also accessing information that includes values of a measure of the sub-volumes as a function of the calculated doses and the calculated dose rates. A graphical user interface includes a
(Continued)

rendering that is based on the calculated doses, the calculated doses rates, and the values of the measure.

22 Claims, 31 Drawing Sheets
(23 of 31 Drawing Sheet(s) Filed in Color)

(52) U.S. Cl.
CPC ............... *A61N 2005/1087* (2013.01); *A61N 2005/1089* (2013.01)

(56) References Cited

U.S. PATENT DOCUMENTS

| | | | |
|---|---|---|---|
| 2011/0135058 A1* | 6/2011 | Sgouros | A61N 5/103 |
| | | | 378/65 |
| 2017/0087383 A1* | 3/2017 | Peltola | A61N 5/1031 |
| 2018/0311509 A1* | 11/2018 | Sjölund | A61N 5/1031 |
| 2019/0022407 A1 | 1/2019 | Abel et al. | |
| 2019/0060667 A1* | 2/2019 | Vanderstraeten | A61N 5/1038 |
| 2019/0083814 A1* | 3/2019 | Tallinen | A61N 5/1045 |

* cited by examiner

1300

"80% of the PTV receives a dose above 60 Gy and a dose rate above 40 Gy/s"

2600

2700

CORRELATION OF DOSE AND DOSE RATE INFORMATION TO VOLUME FOR RADIATION TREATMENT PLANNING

REFERENCE TO PROVISIONAL APPLICATION

This application claims priority to the U.S. Provisional Application filed Jun. 23, 2020, Ser. No. 63/043,027, by P. Lansonneur et al., entitled "Correlation of Dose and Dose Rate Information to Volume for Radiation Treatment Planning," which is hereby incorporated by reference in its entirety.

BACKGROUND

The use of radiation therapy to treat cancer is well known. Typically, radiation therapy involves directing a beam of high energy proton, photon, ion, or electron radiation ("therapeutic radiation") into a target or volume in a treatment target (e.g., a volume that includes a tumor or lesion).

Before a patient is treated with radiation, a treatment plan specific to that patient is developed. The plan defines various aspects of the therapy using simulations and optimizations that may be based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A relatively recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to a high radiation dose for only a very short period of time.

FLASH RT introduces important interdependencies that are not captured by conventional radiation treatment planning. Current tools such as dose-volume histograms and dose-rate volume histograms do not capture the interdependence of dose and dose rate. For example, developing a dose rate distribution for a high-quality plan is not trivial from a clinician's perspective because normal tissue might benefit from a low dose rate in certain regions if the dose is minimized in these regions. Also, for example, irradiating a restricted number of spots in a treatment volume may lead to high dose rate delivery but low dose homogeneity at the level of the tumor, while on the other hand, plan quality could be improved by increasing the number of spots at the cost of lowering the dose rate.

SUMMARY

Embodiments according to the present invention thus provide an improved method of generating and evaluating radiation treatment plans, and improved radiation treatment based on those plans, for FLASH radiation therapy (FLASH RT).

In embodiments, a computer-implemented method for planning radiation treatment includes accessing information that includes calculated doses and calculated dose rates for sub-volumes in a treatment target (e.g., any number of voxels in any three-dimensional shape, constituting a volume of sub-volumes), and also accessing information that includes values of a measure (e.g., a number, percentage, or fraction) of the sub-volumes as a function of the calculated doses and the calculated dose rates. A graphical user interface (GUI) that includes a rendering (e.g., a visual display) that is based on the calculated doses, the calculated doses rates, and the values of the measure is then displayed.

In embodiments, the rendering includes a visualization (e.g., a graphic element) of a dose-volume histogram as a first dimension (e.g., an element or aspect of the visualization, or a spatial dimension in virtual space) of the GUI, a visualization of a dose rate-volume histogram as a second dimension of the GUI, and a visualization of the values of the measure as a third dimension of the GUI. For example, the rendering can include a visualization of the calculated dose rate per sub-volume, a visualization of a calculated dose per sub-volume, and a visualization of the measure per sub-volume. In embodiments, the rendering also includes a visualization of a prescription dose and a prescription dose rate. In embodiments, the rendering also includes a visualization of normal tissue complication probability per sub-volume. In embodiments, the rendering also includes a visualization of tumor control probability per sub-volume. In embodiments, different attribute values (e.g., color, pattern, gray-scale, alphanumeric text, or brightness) are associated with elements of the visualizations.

Displaying a GUI that visualizes, in a single rendering, calculated doses and calculated dose rates for sub-volumes in a treatment target, and values of a measure of the sub-volumes as a function of the calculated doses and the calculated dose rates, allows a clinician to better evaluate the balance between dose rate and dose homogeneity. In essentially a single glance, a clinician can evaluate the quality of a proposed radiation treatment plan, make changes to the proposed plan, and evaluate the results of the changes.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments according to the invention improve radiation treatment planning and the treatment itself by expanding FLASH RT to a wider variety of treatment platforms and target sites (e.g., tumors). Treatment plans generated as described herein are superior for sparing healthy tissue from radiation in comparison to conventional techniques for FLASH dose rates by optimizing the balance between the dose rate delivered to unhealthy tissue (e.g., a tumor) in a volume in a treatment target and the dose rate delivered to surrounding healthy tissue. When used with FLASH dose rates, management of patient motion is simplified because the doses are applied in a short period of time (e.g., less than a second). Treatment planning, while still a complex task, is improved relative to conventional treatment planning. In addition to these benefits, a GUI facilitates treatment planning by allowing a planner to readily visualize key elements of a proposed treatment plan, to readily visualize the effects on those elements of changes to the proposed plan and compare different plans, and to define and establish optimization objectives.

In summary, embodiments according to this disclosure pertain to generating and implementing a treatment plan that is the most effective (relative to other plans) and with the least (or most acceptable) side effects (e.g., a lower dose rate outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans, fewer computational resources are needed and consumed, meaning also that computer resources are freed up to perform other tasks.

In addition to radiation therapy techniques such as IMRT and IMPT, embodiments according to the invention can be used in spatially fractionated radiation therapy including high-dose spatially fractionated grid radiation therapy, minibeam radiation therapy, and microbeam radiation therapy.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The patent or application file contains at least one drawing executed in color. Copies of this patent or patent application publication with color drawing(s) will be provided by the Office upon request and payment of the necessary fee.

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
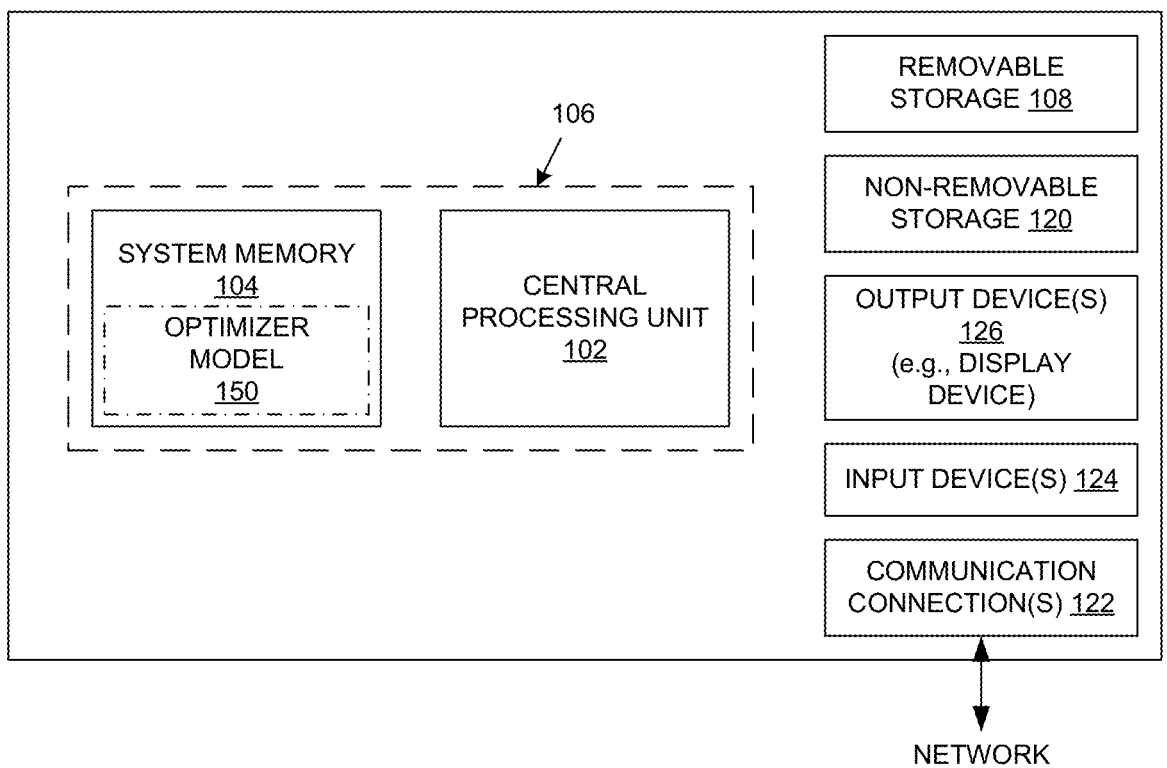
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "generating," "representing," "applying," "indicating," "storing," "using," "adjusting," "including," "computing," "calculating," "determining," "visualizing," "displaying," "rendering," "associating," "binning," or "rounding," or the like, refer to actions and processes (e.g., the flowcharts of FIGS. 6 and 8-10) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow includes terms such as "dose," "dose rate," "energy," etc. Unless otherwise noted, a value is associated with each such term. For example, a dose has a value and can have different values. For simplicity, the term "dose" may refer to a value of a dose, for example, unless otherwise noted or apparent from the discussion.

Portions of the detailed description that follows are presented and discussed in terms of methods. Although steps and sequencing thereof are disclosed in figures herein (e.g., FIGS. 6 and 8-10) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Radiation Treatment Planning Using Different Types of Histograms

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included. A display device may be, for example, a cathode ray tube display, a light-emitting diode display, or a liquid crystal display.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
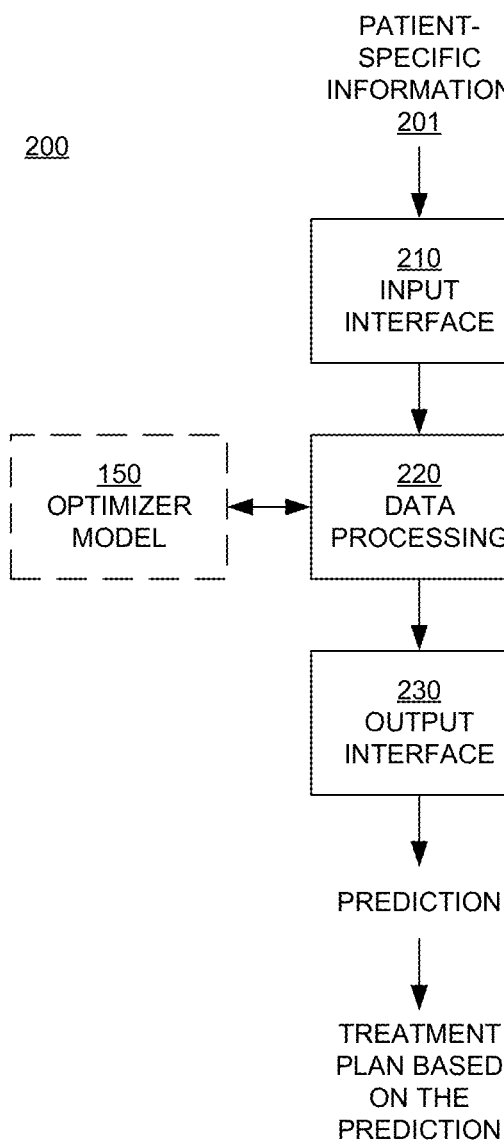
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. In embodiments, the optimizer model 150 yields a prediction result, and a treatment plan based on the prediction result can then be generated.

Figure 3:
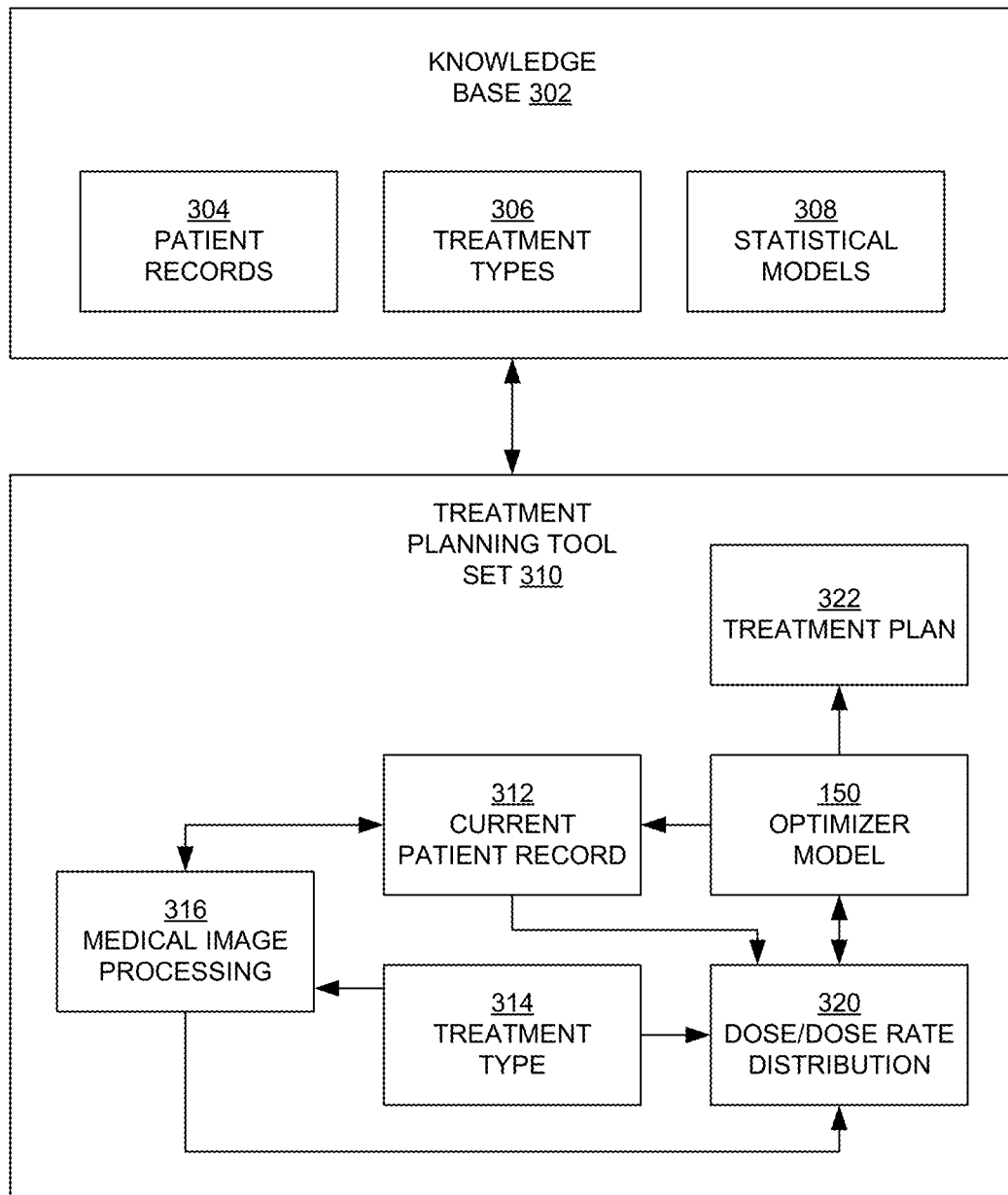
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose and/or dose rate can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 150.

In embodiments according to the present invention, the optimizer model 150 uses a dose prediction model to provide, for example, a 3D dose distribution, fluences, and dose rates, and associated dose-volume histograms (DVHs) and dose rate-volume histograms (DRVHs).

The discussion to follow refers to beams, volumes, doses, dose rates, and other elements or values. The discussion below is in the context of modeled elements and calculated values in the treatment planning tool set 310 and the optimizer model 150 (FIG. 3), unless otherwise noted or made clear in the discussion.

Figure 4:
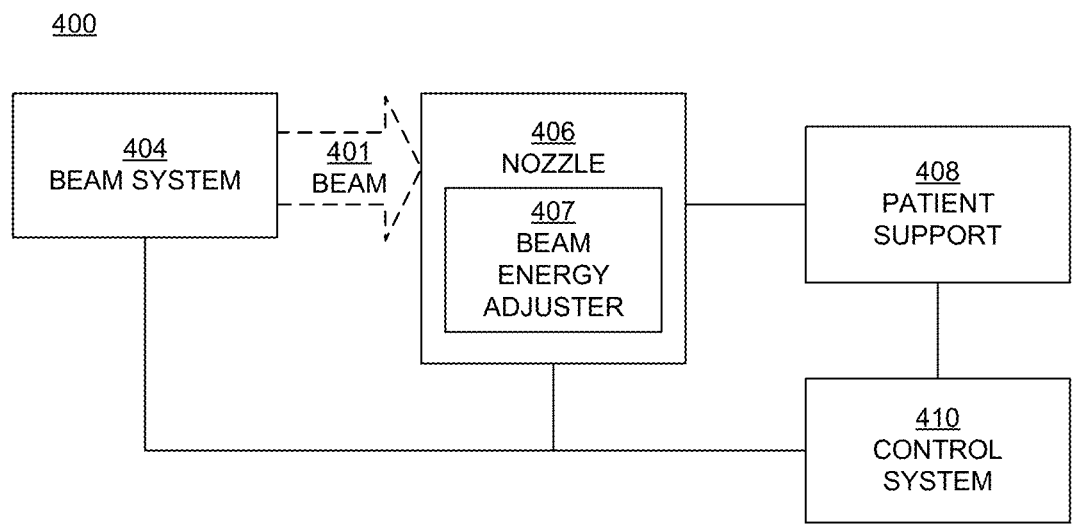
FIG. 4 is a block diagram showing selected components of a radiation therapy system upon which embodiments according to the present invention can be implemented.

FIG. 4 is a block diagram showing selected components of a radiation therapy system 400 upon which embodiments according to the present invention can be implemented. In the example of FIG. 4, the system 400 includes a beam system 404 and a nozzle 406.

The beam system 404 generates and transports a beam 401. The beam 401 can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam system in a direction toward and into a nozzle 406. In embodiments, the radiation therapy system may include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 is used to aim the beam toward various locations (a volume in a treatment target) (e.g., a volume in a patient) supported on the patient support device 408 (e.g., a chair or table) in a treatment room. A volume in a treatment target may be an organ, a portion of an organ (e.g., a volume or region within the organ), a tumor, diseased tissue, or a patient outline. A volume in a treatment target may include both unhealthy tissue (e.g., a tumor) and healthy tissue. A volume in a treatment target may be divided (virtually) into a number of voxels. A sub-volume can include a single voxel or multiple voxels.

The nozzle 406 may be mounted on or a part of a gantry that can be moved relative to the patient support device 408, which may also be moveable. In embodiments, the beam system 404 is also mounted on or is a part of the gantry. In another embodiment, the beam system is separate from (but in communication with) the gantry.

The control system 410 of FIG. 4 receives and implements a prescribed radiation treatment plan. In embodiments, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and/or shape of the beam, according to data it receives and according to the prescribed radiation treatment plan.

As noted above, the beam 401 entering the nozzle 406 has a specified energy. Thus, in embodiments according to the present disclosure, the nozzle 406 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth-dose curve of the beam, depending on the type of beam. For example, for a proton beam or an ion beam that has a Bragg peak, the beam energy adjuster can control the location of the Bragg peak in the volume in a treatment target. In various embodiments, the beam energy adjuster 407 includes a range modulator, a range shifter, or both a range modulator and a range shifter.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

The beam 401 can have virtually any regular or irregular cross-sectional (e.g., beam's eye view) shape. For example, the shape of the beam 401 can be defined using an MLC that blocks a portion or portions of the beam. Different beams can have different shapes.

In embodiments, the beam 401 includes a number of beam segments or beam lets (that also may be referred to as spots). A maximum energy (e.g., 80 MeV) is specified for the beam 401, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The defined energy level or intensity can be realized for each beam segment using the beam energy adjuster 407.

Each beam segment can deliver a relatively high dose rate (a relatively high dose in a relatively short period of time). For example, each beam segment can deliver at least 40 grays (Gy) in less than one second, and may deliver as much as 120 Gy per second or more.

In operation, in embodiments, the beam segments are delivered sequentially. For example, a first beam segment is delivered to the volume in a treatment target (turned on) and then turned off, then a second beam segment is turned on then off, and so on. Each beam segment may be turned on for only a fraction of a second (e.g., on the order of milliseconds).

A single beam may be used and applied from different directions and in the same plane or in different planes. Alternatively, multiple beams may be used, in the same plane or in different planes. The directions and/or numbers of beam can be varied over a number of treatment sessions (that is, fractionated in time) so that a uniform dose is delivered across the volume in the treatment target. The number of beams delivered at any one time depends on the number of gantries or nozzles in the radiation treatment system (e.g., the radiation treatment system 400 of FIG. 4) and on the treatment plan.

In embodiments according to the present invention, a DRVH (which is different from a DVH) is generated for a volume in a treatment target. The DRVH can be generated based on a proposed radiation treatment plan. The DRVH can be stored in computer system memory and used to generate a final radiation treatment plan that will be used to treat a patient. Values of parameters that can have an effect on dose rate can be adjusted until the DRVH satisfies objectives of or associated with treatment of the patient.

Figure 5A:
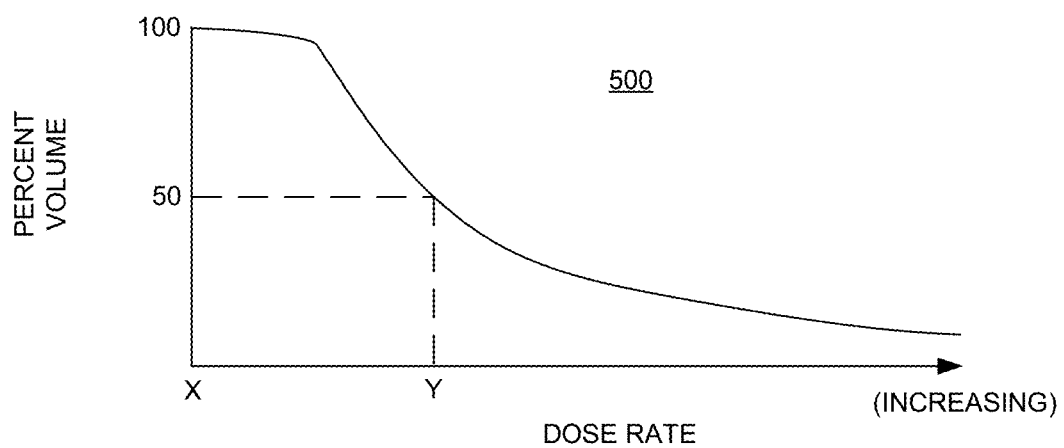
FIGS. 5A and 5B illustrate examples of dose rate-volume histograms in an embodiment according to the present invention.

FIG. 5A illustrates an example of a DRVH 500 in an embodiment according to the present invention. The DRVH plots a cumulative dose rate-to-volume in a treatment target frequency distribution that summarizes the simulated dose rate distribution within a volume in a treatment target of interest that would result from a proposed radiation treatment plan. The simulated dose rate distribution can be determined using the optimizer model 150 of FIG. 1. The DRVH indicates dose rates and percentages of the volume in a treatment target that receive the dose rates. For example, as shown in FIG. 5A, 100 percent of the volume in a treatment target receives a dose rate of X or more (at least X), 50 percent of the volume in a treatment target receives a dose rate of Y or more (at least Y), and so on. The DRVH 500 can be displayed as or as part of a graphical user interface (GUI) (see the discussion below).

Figure 5B:
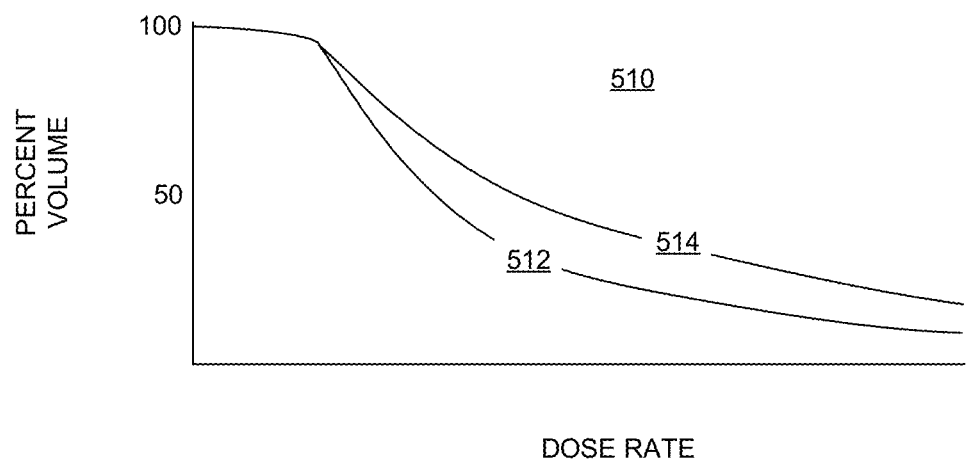
Figure 5C:
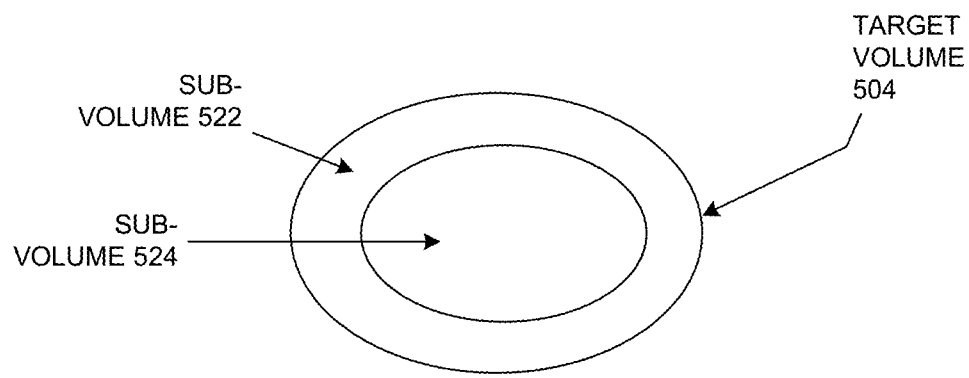
FIG. 5C illustrates sub-volumes in a volume in a treatment target in an embodiment according to the present invention.

The volume in a treatment target may include different organs, for example, or it may include both healthy tissue and unhealthy tissue (e.g., a tumor). Accordingly, with reference to FIGS. 5B and 5C, the DRVH 510 includes multiple curves 512 and 514, showing the simulated dose rate distribution for a first sub-volume 522 of the volume 504 in a treatment target (e.g., for one organ, or for the healthy tissue) and the simulated dose rate distribution for a second sub-volume 524 (e.g., for a second organ, or for the unhealthy tissue), respectively. More than two simulated dose rate distributions can be included in a DRVH. The DRVH 510 can be displayed as or as part of a GUI.

In embodiments according to the present invention, an irradiation time-volume histogram (which is different from, but may be used with, a DVH and/or a DRVH) is generated for the volume in a treatment target. The irradiation time-volume histogram can be stored in computer system memory and used to generate a radiation treatment plan, in combination with or in lieu of a DVH and/or a DRVH.

Figure 5D:
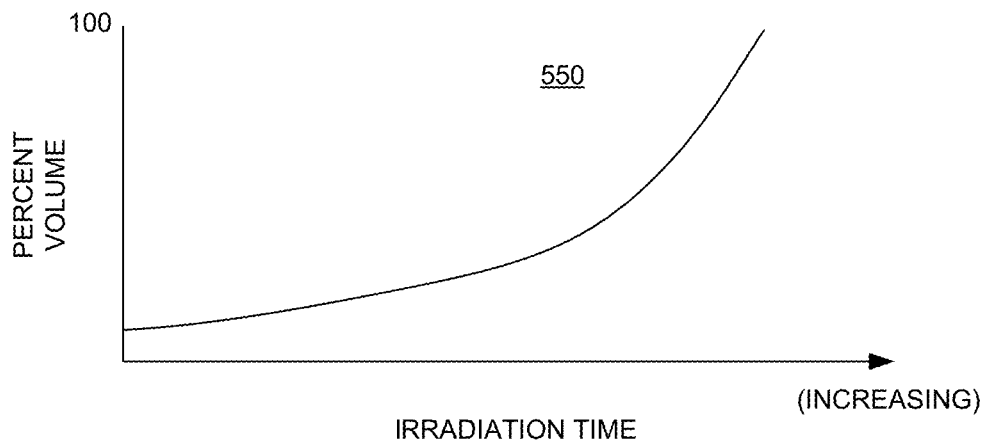
FIG. 5D illustrates an example of an irradiation time-volume histogram in an embodiment according to the present invention.

FIG. 5D illustrates an example of an irradiation time-volume histogram 550 in an embodiment according to the present invention. The irradiation time-volume histogram plots a cumulative irradiation time-to-volume in a treatment target frequency distribution that summarizes the simulated irradiation time distribution within a volume in a treatment target that would result from a proposed radiation treatment plan. The simulated irradiation time distribution can be determined using the optimizer model 150 of FIG. 1. The irradiation time-volume histogram indicates irradiation times (lengths of times) and percentages of the volume that are irradiated for those lengths of time. The DRVH 550 can be displayed as or as part of a GUI.

Figure 6:
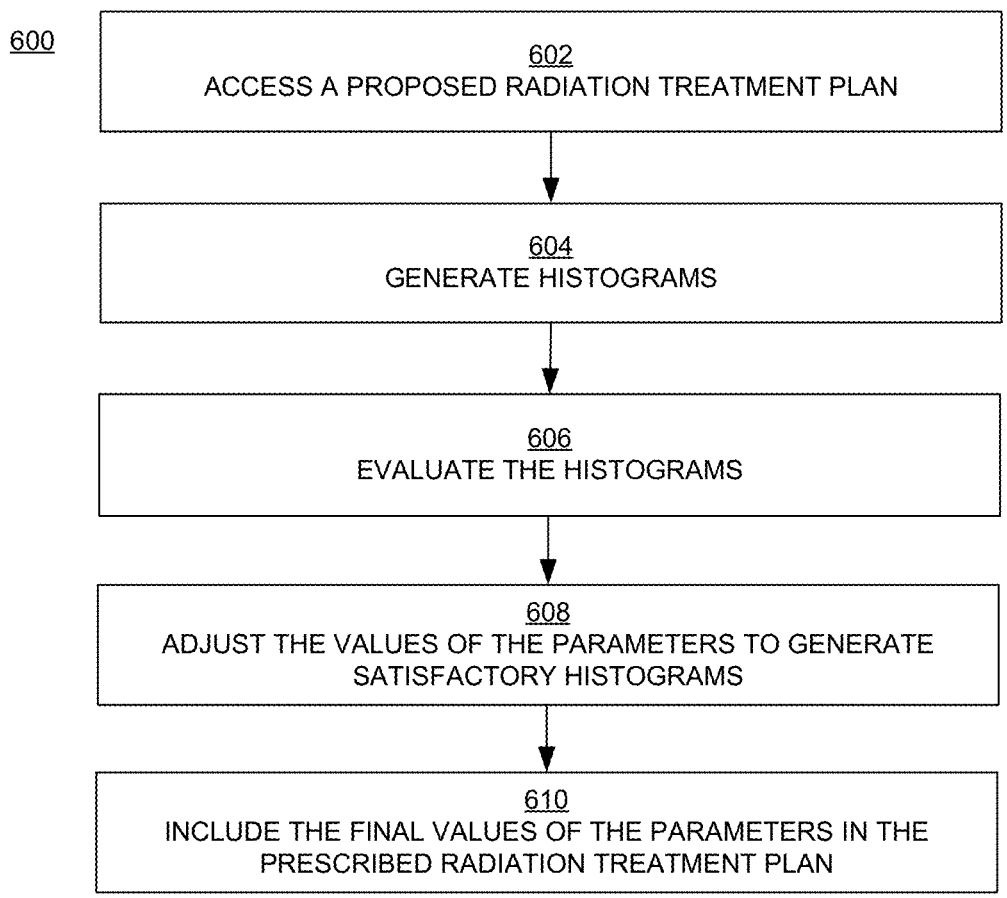
FIG. 6 is a flowchart of an example of computer-implemented operations for radiation treatment planning in embodiments according to the present invention.
Figure 7:
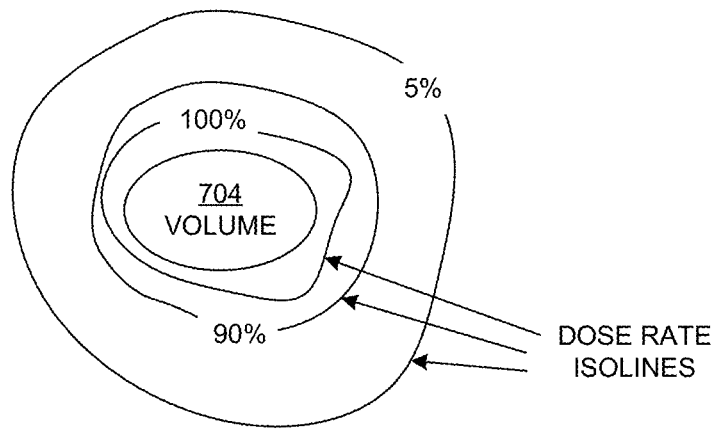
FIG. 7 illustrates an example of dose rate isolines in embodiments according to the present invention.

FIG. 6 is a flowchart 600 of an example of computer-implemented operations for radiation treatment planning including generating a DVH, a DRVH, or an irradiation time-volume histogram in embodiments according to the present invention. The flowchart 600 can be implemented as computer-executable instructions (e.g., the optimizer model 150 of FIG. 1) residing on some form of computer-readable storage medium (e.g., in memory of the computer system 100 of FIG. 1).

In block 602 of FIG. 6, a proposed radiation treatment plan is defined (e.g., using the optimizer model 150 of FIGS. 1 and 2), stored in a computer system memory, and accessed from that memory. The proposed radiation treatment plan includes values of parameters that can affect dose and dose rate, as well as other parameters. The parameters that can affect dose and dose rate include, but are not limited to, a number of irradiations of the volume in a treatment target, a duration of each of the irradiations (irradiation times), and a dose deposited in each of the irradiations. The parameters may also include directions of beams to be directed into the volume in a treatment target, and beam energies for each of the beams. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). If the volume in a treatment target is divided into sub-volumes or voxels, then the values of the parameters can be on a per-sub-volume or per-voxel basis (e.g., a value per sub-volume or voxel).

Appropriate dose threshold curve(s) (e.g., normal tissue sparing dose versus dose rate or irradiation time) can be utilized in the optimization model 150 (FIG. 3) to establish dose limits for radiation treatment planning. For example, the appropriate (e.g., tissue-dependent) dose threshold curve can be used to determine beam directions (gantry angles) and beam segment weights. That is, parameters that affect dose can be adjusted during radiation treatment planning so that the limits in the dose threshold curve are satisfied. The dose threshold curves can be tissue-dependent. For instance, the dose threshold curve for the lungs may be different from that for the brain.

Dose limits can include, but are not limited to: a maximum limit on irradiation time for each sub-volume (voxel) in the target (e.g., for each voxel of target tissue, treatment time less than x1 seconds); a maximum limit on irradiation time for each sub-volume (voxel) outside the target (e.g., for each voxel of normal tissue, treatment time less than x2 seconds; x1 and x2 may be the same or different); a minimum limit on dose rate for each sub-volume (voxel) in the target (e.g., for each voxel of target tissue, dose rate greater than y1 Gy/sec); and a minimum limit on dose rate for each sub-volume (voxel) outside the target (e.g., for each voxel of normal tissue, dose rate greater than y2 Gy/sec; y1 and y2 may be the same or different). In general, the limits are intended to minimize the amount of time that normal tissue is irradiated.

In block 604, in an embodiment, a DVH and a DRVH are generated based on the values of the parameters in the proposed radiation treatment plan. A dose and a dose rate can be determined per sub-volume or voxel. The dose rate is the sum of the dose deposited in each irradiation divided by the sum of the durations of the irradiation. The dose rate can be determined and recorded using a fine time index (e.g., time increments on the order of a millisecond); that is, for example, the dose to each sub-volume or voxel can be recorded for time increments on the order of per-millisecond per beam and per fraction. The dose and dose rate are cumulative. The cumulative dose and dose rate for some portions (e.g., sub-volumes or voxels) of the volume in a treatment target may be higher than other portions, depending on the beam directions and energies, for example. The dose and dose rate per sub-volume or voxel can be calculated to include ray tracing (and Monte Carlo-like simulations), where each beam particle is tracked to determine the primary, secondary, etc., scatters for each particle to get a realistic voxel-based or sub-volume-based dose rate over the course of each irradiation.

In an embodiment, an irradiation time-volume histogram is generated. An irradiation time-volume histogram can be generated essentially in the same manner as that just described for generating a DRVH.

In block 606, the DVH, the DRVH, and/or the irradiation time-volume histogram can be evaluated by determining whether or not objectives (e.g., clinical goals) that are specified for treatment of a patient are satisfied by the proposed radiation treatment plan. The clinical goals or objectives may be expressed in terms of a set of quality metrics, such as target homogeneity, critical organ sparing, and the like, with respective target values for the metrics. Another way to evaluate the histograms is a knowledge-based approach that incorporates and reflects present best practices gathered from multiple previous, similar treatments of other patients. Yet another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and if none of the metrics can be improved without worsening at least one of the other metrics.

As mentioned above, for FLASH RT, dose rates of at least 40 Gy in less than one second, and as much as 120 Gy per second or more, may be used. Thus, another way to evaluate a DVH and a DRVH is to define a dose threshold value and a dose rate threshold value based on the FLASH RT dose rates, and to also specify threshold values in a treatment target for dose and dose rate. A DVH and a DRVH can be evaluated by determining whether a measure (e.g., fraction, number, or percentage of sub-volumes or voxels) of the volume in a treatment target satisfies the dose and dose rate threshold values. For example, a dose-rate volume histogram may be considered to be satisfactory if 60 percent of the volume in a treatment target (specifically, the portion of the volume in a treatment target that includes the unhealthy tissue) receives a dose rate of at least 50 Gy per second.

In block 608 of FIG. 6, some or all of the parameter values for the proposed radiation treatment plan can be iteratively adjusted to generate different DVHs, DRVHs, and/or irradiation time-volume histograms, to determine a final set of parameter values that produce a histogram (or histograms) that results in a prescribed (final) radiation treatment plan that best satisfies the objectives (clinical goals) for treatment of the patient or that satisfies the threshold values described above.

In block 610, the final set of parameter values is then included in the prescribed radiation treatment plan used to treat the patient.

Generally speaking, embodiments according to the invention optimize a radiation treatment plan based on dose, dose rate, and/or irradiation time. This is not to say that treatment plan optimization is based solely on dose, dose rate, and/or irradiation time.

Correlation of Dose, Dose Rate, and Volume for Treatment Planning

Figure 8:
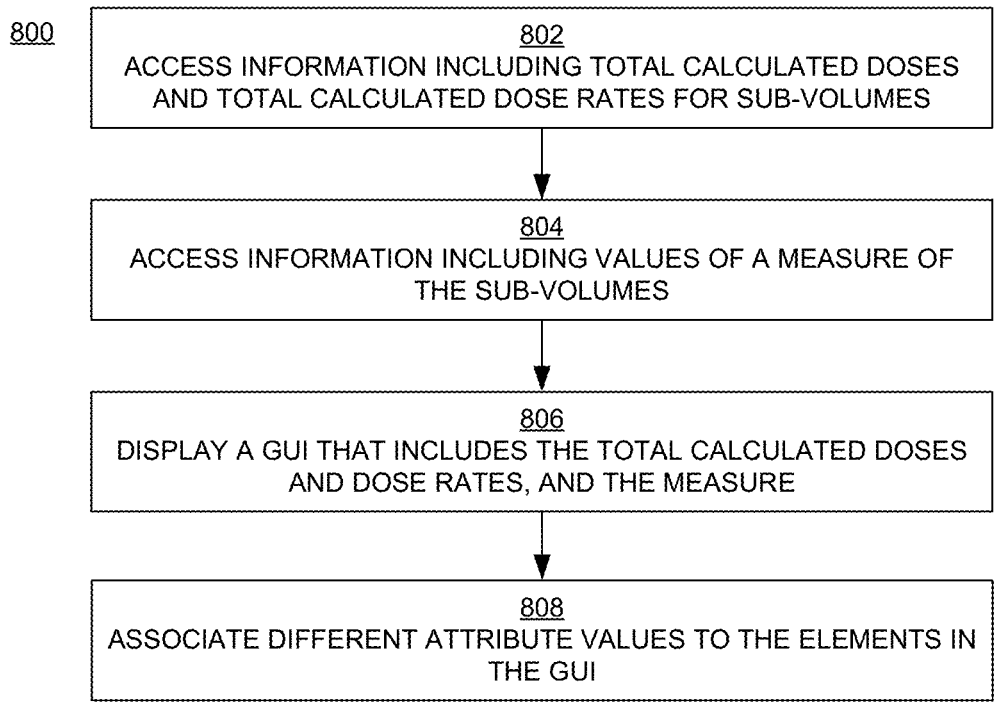
FIGS. 8, 9, and 10 are flowcharts of an example of computer-implemented operations for planning radiation treatment in embodiments according to the present invention.
Figure 9:
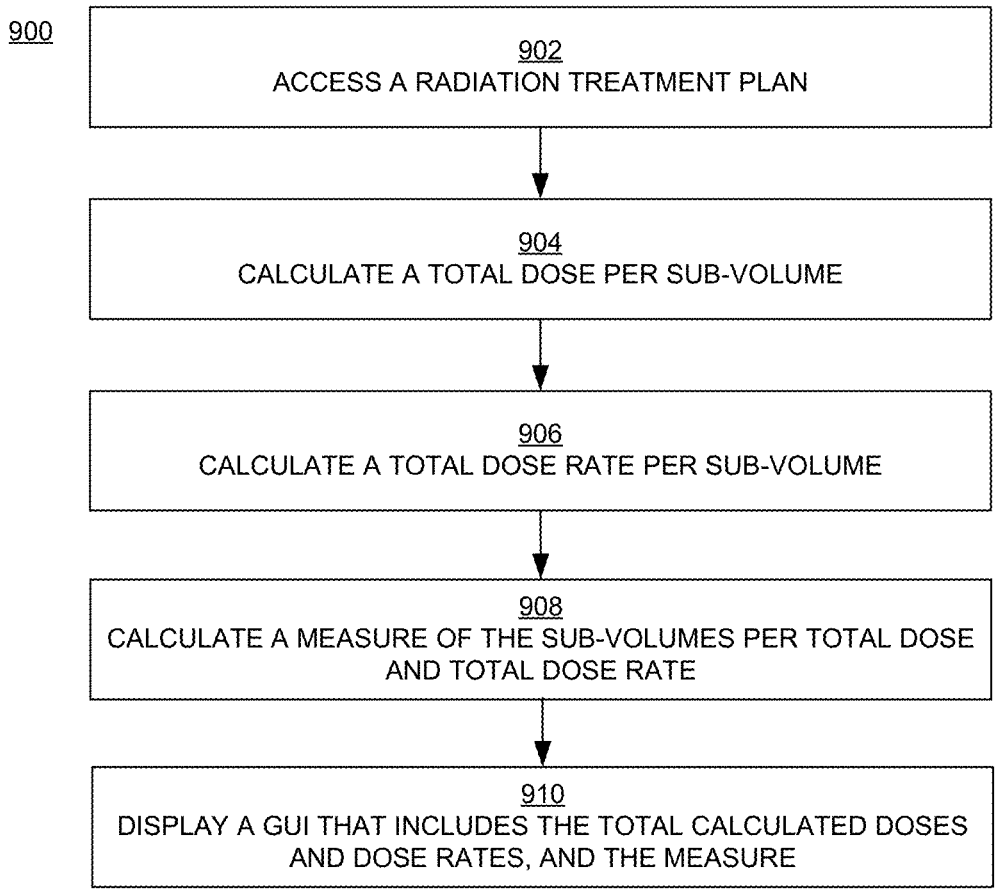
Figure 10:
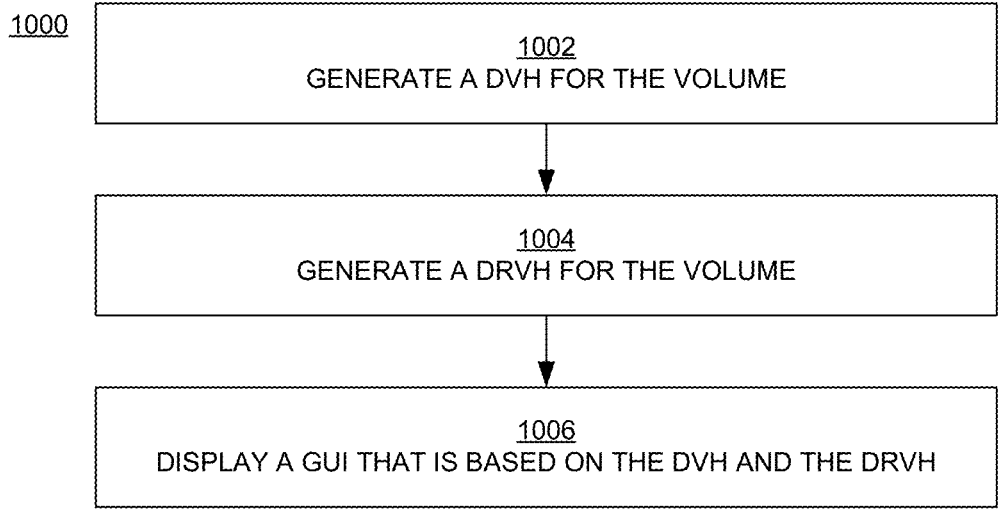

FIGS. 8, 9, and 10 are flowcharts 800, 900, and 1000 (800-1000) of examples of computer-implemented methods for planning radiation treatment in embodiments according to the present invention. The flowcharts 800-1000 can be implemented as computer-executable instructions (e.g., the optimizer model 150 of FIG. 1) residing on some form of computer-readable storage medium (e.g., in memory of the computer system 100 of FIG. 1). In these embodiments, as a result of the disclosed methods, a GUI is generated and displayed. The GUI visualizes, in a single rendering, calculated doses (e.g., total calculated doses) and calculated dose rates for sub-volumes in a treatment target, and values of a measure of the sub-volumes as a function of the calculated doses and the calculated dose rates, for example. Examples of a GUI in accordance with the present invention are provided in FIGS. 11, 12, 13A, 13B, and 14-28, 29A, 29B, 30A, 30B, and 31-35.

In block 802 of FIG. 8, information that includes calculate doses (e.g., total calculated doses) and calculated dose rates for sub-volumes in a treatment target (e.g., any number of voxels in any three-dimensional shape, constituting a volume of sub-volumes), and also information that includes values of a measure (e.g., a number, percentage, or fraction) of the sub-volumes as a function of the calculated doses and the calculated dose rates, are accessed from computer system memory.

In block 804, information that includes values of a measure (e.g., a number, percentage, or fraction) of the sub-volumes as a function of the calculated doses (e.g., total calculated doses) and the calculated dose rates is also accessed from computer system memory.

In block 806, a GUI that includes a rendering (e.g., a visual display) that is based on the calculated doses, the calculated doses rates, and the values of the measure, is displayed on the display device 126 (FIG. 1) of a computer system.

In block 808 of FIG. 8, different attribute values (e.g., color, pattern, gray-scale, alphanumeric text, or brightness) are associated with elements of the visualizations in the GUI.

With reference now to FIG. 9, in block 902, a radiation treatment plan is accessed from computer system memory. The radiation treatment plan includes, for example, a number of beams to be directed at and into a volume in a treatment target, directions of the beams, and a range of dose rates for each of the beams.

In block 904, a dose (e.g., total dose) per sub-volume is calculated using the number and directions of the beams and the range of dose rates.

In block 906, a dose rate per sub-volume is calculated using the number and directions of the beams and the range of dose rates.

In block 908, for different levels or ranges (e.g., bins) of dose (e.g., total dose) and different levels or ranges (e.g., bins) of dose rate, a value of a measure (e.g., number, fraction, or percentage) of the sub-volumes that are calculated to receive at least a respective level of dose (e.g., total dose) and at least a respective level of dose rate is determined.

In block 910, a GUI that includes a rendering (e.g., a visual display) that is based on the calculated doses, the calculated doses rates, and the values of the measure, is displayed on the display device 126 (FIG. 1).

With reference now to FIG. 10, in block 1002, a DVH for a volume in a treatment target is generated.

In block 1004, a DRVH for the volume is generated.

In block 1006, a GUI that includes a combined rendering of the DVH and the DRVH is displayed on the display device 126 (FIG. 1) of a computer system. The combined rendering visualizes a measure of the volume that is calculated to receive a given dose as a function of dose rate and also a measure of the volume that is calculated to receive a given dose rate as a function of dose.

In embodiments, the rendering in the GUI that is generated and displayed as described above includes a visualization (e.g., a graphic element) of a DVH as a first dimension (e.g., an element or aspect of the visualization, or a spatial dimension in virtual space) of the GUI, a visualization of a DRVH as a second dimension of the GUI, and a visualization of the values of the measure as a third dimension of the GUI. For example, the rendering can include a visualization of the calculated dose rate per sub-volume, a visualization of a calculated dose (e.g., calculated total dose) per sub-volume, and a visualization of the measure per sub-volume. In embodiments, the rendering also includes a visualization of a prescription dose and a prescription dose rate. In embodiments, the rendering also includes a visualization of normal tissue complication probability (NTCP) per sub-volume. In embodiments, the rendering also includes a visualization of tumor control probability (TCP) per sub-volume.

While the operations in FIGS. 6 and 8-10 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

FIGS. 11, 12, 13A, 13B, and 14-28, 29A, 29B, 30A, 30B, and 31-35 illustrate examples of GUIs that can be used to display information associated with a planning radiation treatment in embodiments according to the present invention. The GUIs can be generated using the methods described above, and implemented using computer-executable instructions (e.g., the optimizer model 150 of FIG. 1) residing on some form of computer-readable storage medium (e.g., memory of the computer system 100 of FIG. 1), and can be displayed on the output device 126 of the computer system.

Embodiments according to the present invention are not limited to the GUIs illustrated in FIGS. 11, 12, 13A, 13B, and 14-28, 29A, 29B, 30A, 30B, and 31-35. In general, GUIs in embodiments according to the present invention allow the interdependencies between doses, dose rates, doses and dose rates per volume, and measures of volume as a function of dose and as a function of dose rate, to be readily visualized for radiation treatment planning. The doses, dose rates, etc., in the discussion below are calculated values.

Also, the disclosed GUIs can include information in addition to that included in the examples. For example, the GUIs can also be used to present information such as the directions of beams to be directed into each sub-volume, and beam energies for each of the beams.

In embodiments, drop-down menus or other types of GUI elements (not shown in the figures) can be used to select and establish settings (e.g., attributes, thresholds, etc.) for the GUIs and the type(s) of information to be displayed at any one time.

Also, the GUIs are not necessarily static displays. For example, the information presented in the GUIs can be programmed to change over time or in response to user inputs to illustrate accumulated dose or dose rate versus time. Also, for example, the GUIs can be programmed to present different cross-sectional slices of the volume in a treatment target in sequence to provide a depth dimension to a two-dimensional representation, or to manipulate (e.g., rotate) a virtual three-dimensional representation so that it can be viewed from different perspectives.

Figure 11:
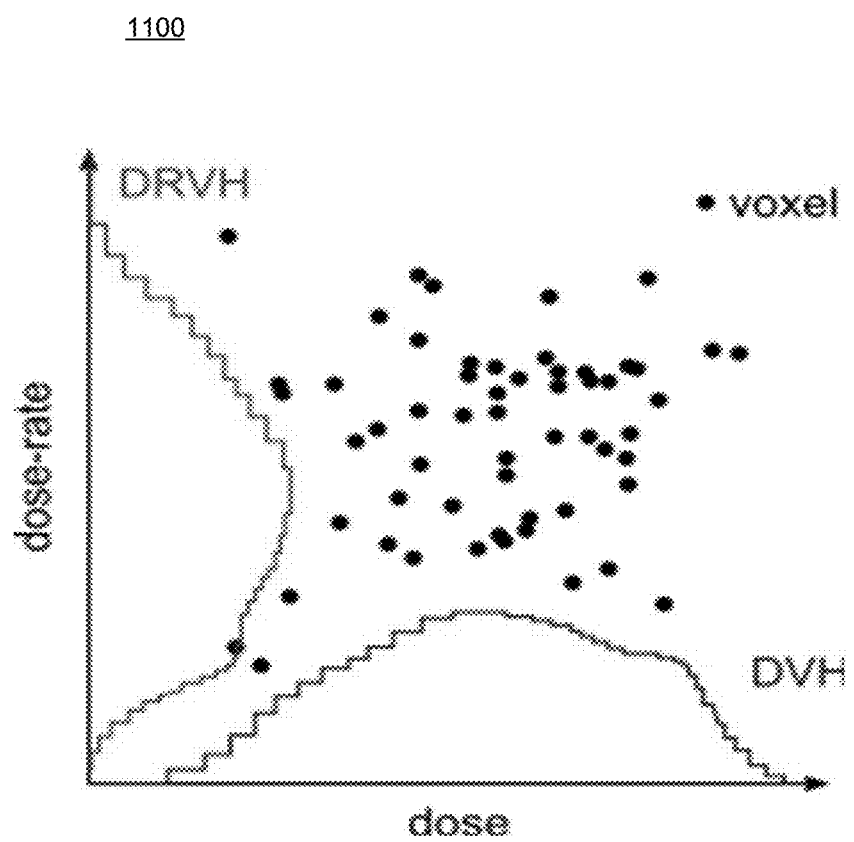
FIGS. 11, 12, 13A, 13B, 14-28, 29A, 29B, 30A, 30B, and 31-35 are examples of graphical user interfaces on a display device and used for planning radiation treatment in embodiments according to the present invention.

In the example of FIG. 11, the GUI 1100 includes a two-dimensional rendering of dose rate versus dose. The dose and dose rate per sub-volume (e.g., voxel) are plotted in the two dimensions. The distribution (measure) of the sub-volumes is projected onto the dose axis to generate a DVH, and is also projected onto the dose rate axis to generate a DRVH.

Figure 12:
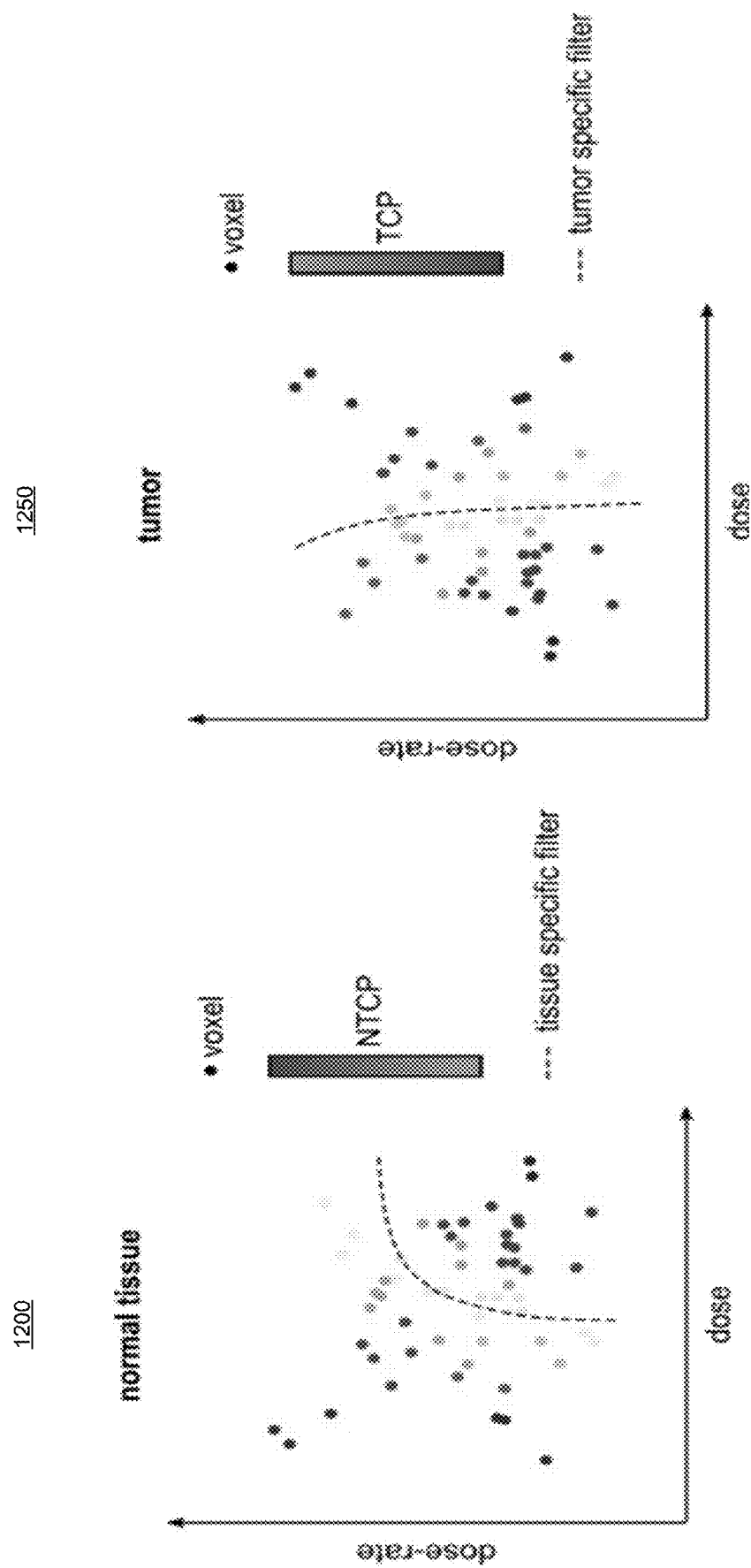

In the example of FIG. 12, the GUI 1200 includes a two-dimensional rendering of dose rate versus dose for normal tissue and for a tumor. The dose and dose rate per sub-volume (e.g., voxel) are visualized (plotted) in the two dimensions. A tissue-specific filter is defined in the plot for the normal tissue, and a tumor-specific filter is defined in the plot for the tumor tissue. Different filters can be defined to account for different tissue responses to dose and dose rate. Voxels can be color-coded to indicate a relative value of NTCP and TCP. In the example of FIG. 12, a color key is included in the GUI 1200 and associated with each of the plots as shown. The color of the voxel in a plot can be compared against the key to indicate the relative value of NTCP or TCP.

Figure 13A:
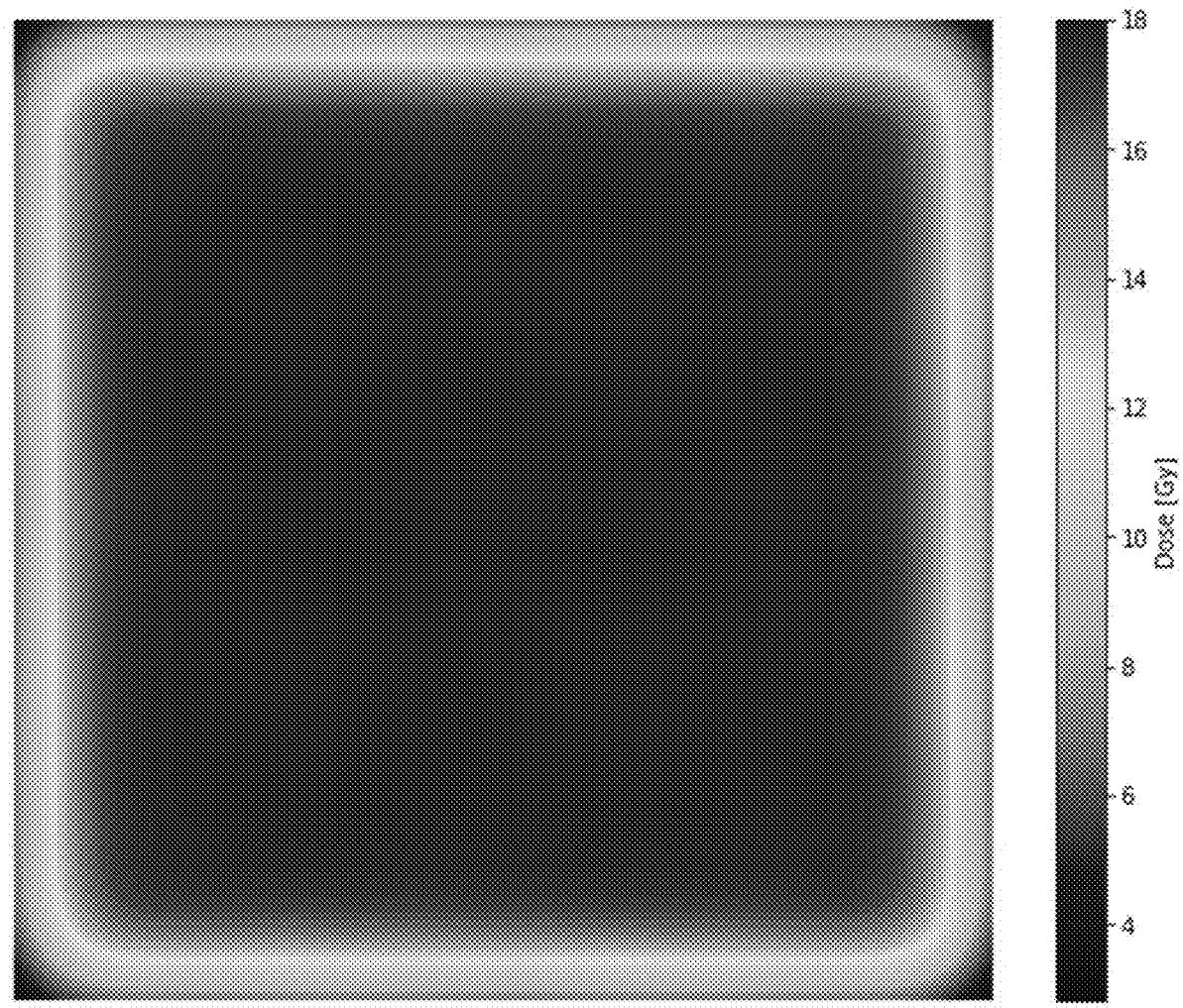
Figure 13B:
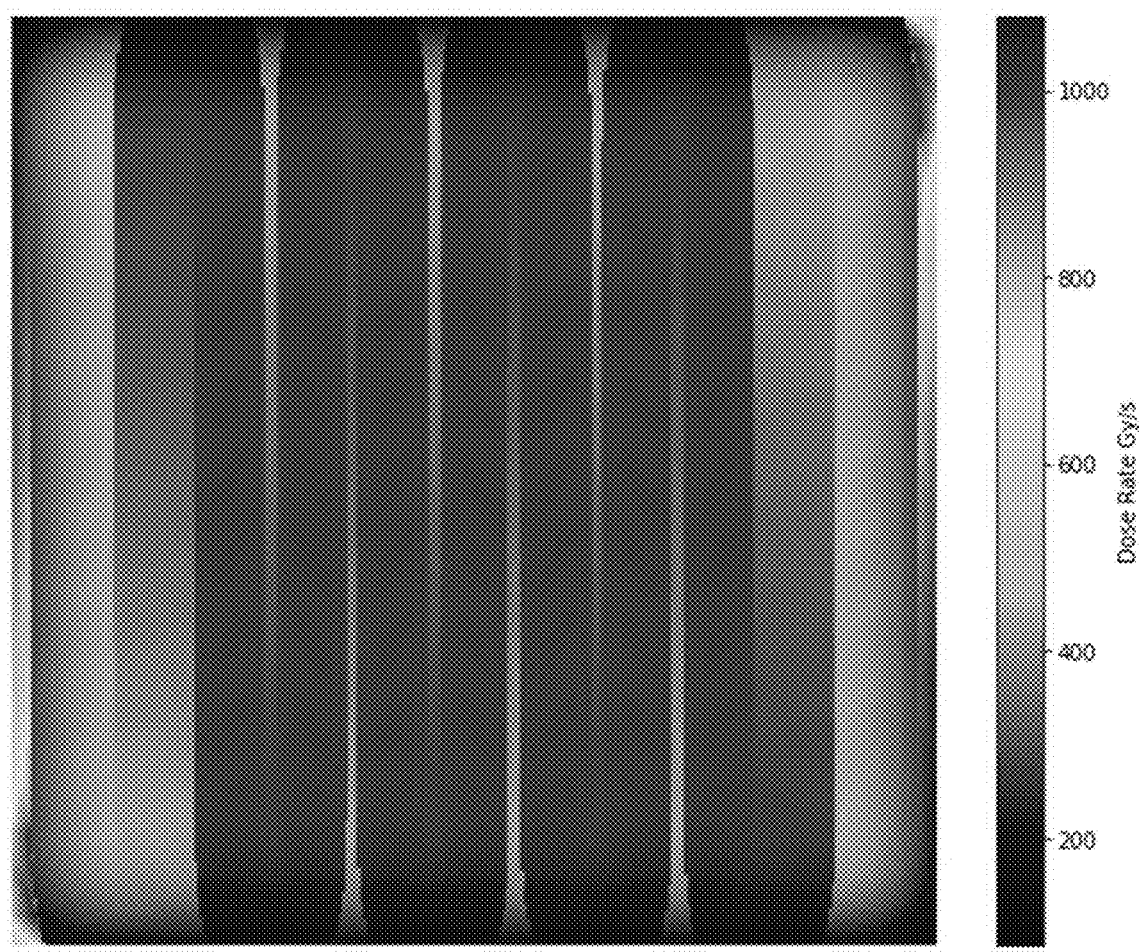

In the example of FIGS. 13A and 13B, the GUI 1300 includes a visualization of dose and dose rate. The GUI 1300 includes a rendering of a plane at the isocenter of a volume of a treatment target. The total area of the plane is divided into different smaller areas, where the size of each smaller area is indicative of (e.g., proportional to) the volume of the target that receives a certain level of dose (FIG. 13A) or dose rate (FIG. 13B). The smaller areas can be color-coded to indicate the level of dose. In the example of FIGS. 13A and 13B, a color key is included in the GUI 1300 to associate colors in the rendering with the different levels of dose and the different levels of dose rate, respectively. The color of each of the smaller areas can be compared to the colors in the key to determine the level of dose/dose rate for each of the smaller areas.

Figure 14:
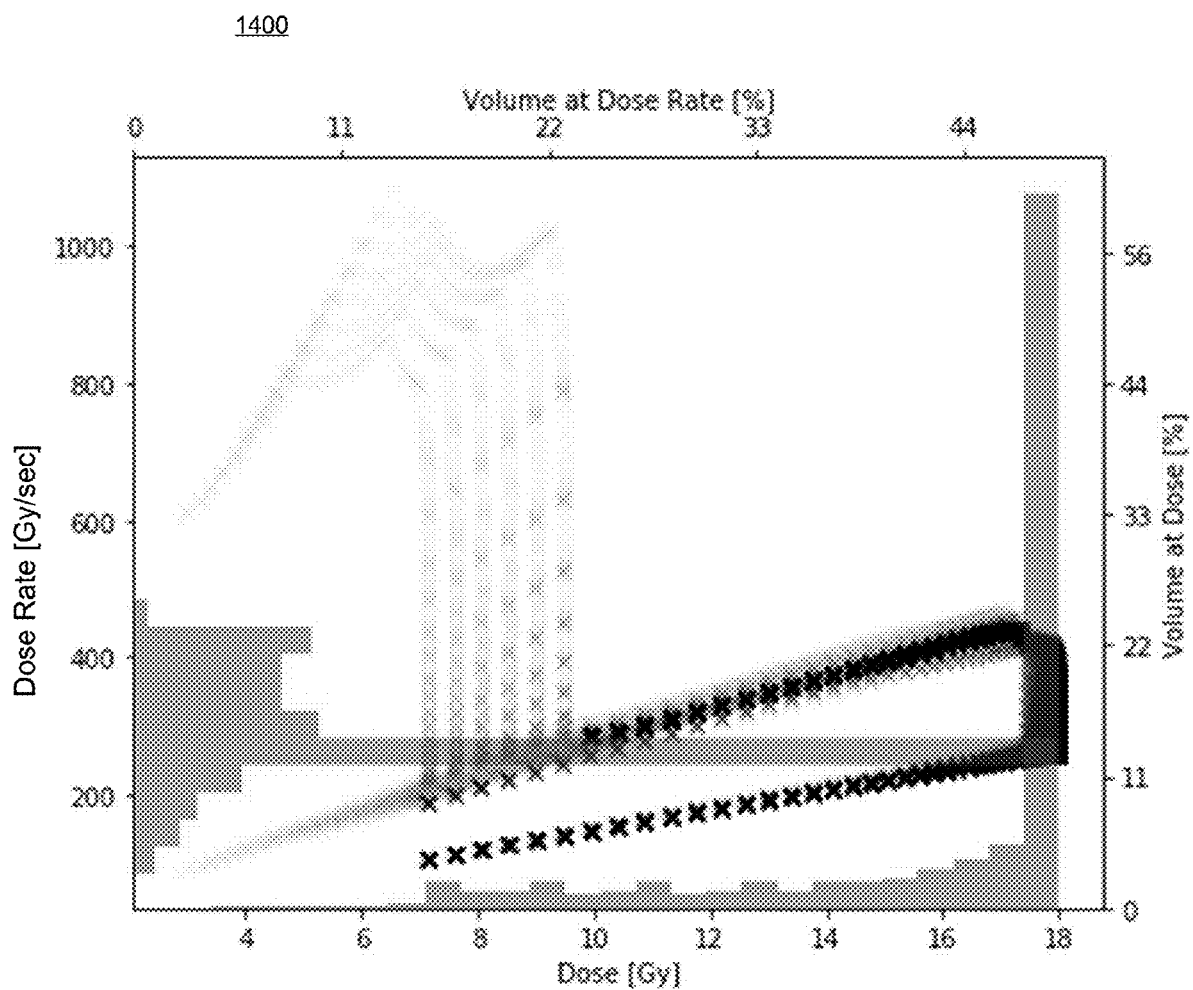

In the example of FIG. 14, the GUI 1400 includes a rendering of dose along one axis and a measure (percentage)

of a volume that receives a given dose along a corresponding axis, and of dose rate along another axis and a percentage of the volume that receives a given dose rate along a corresponding axis. The GUI 1400 is useful for visualizing and identifying qualitative trends. In this figure, each "X" represents one voxel that has both a dose and a dose rate. Each "X" has a certain transparency such that the density of points in the figure can be visualized.

Figure 15:
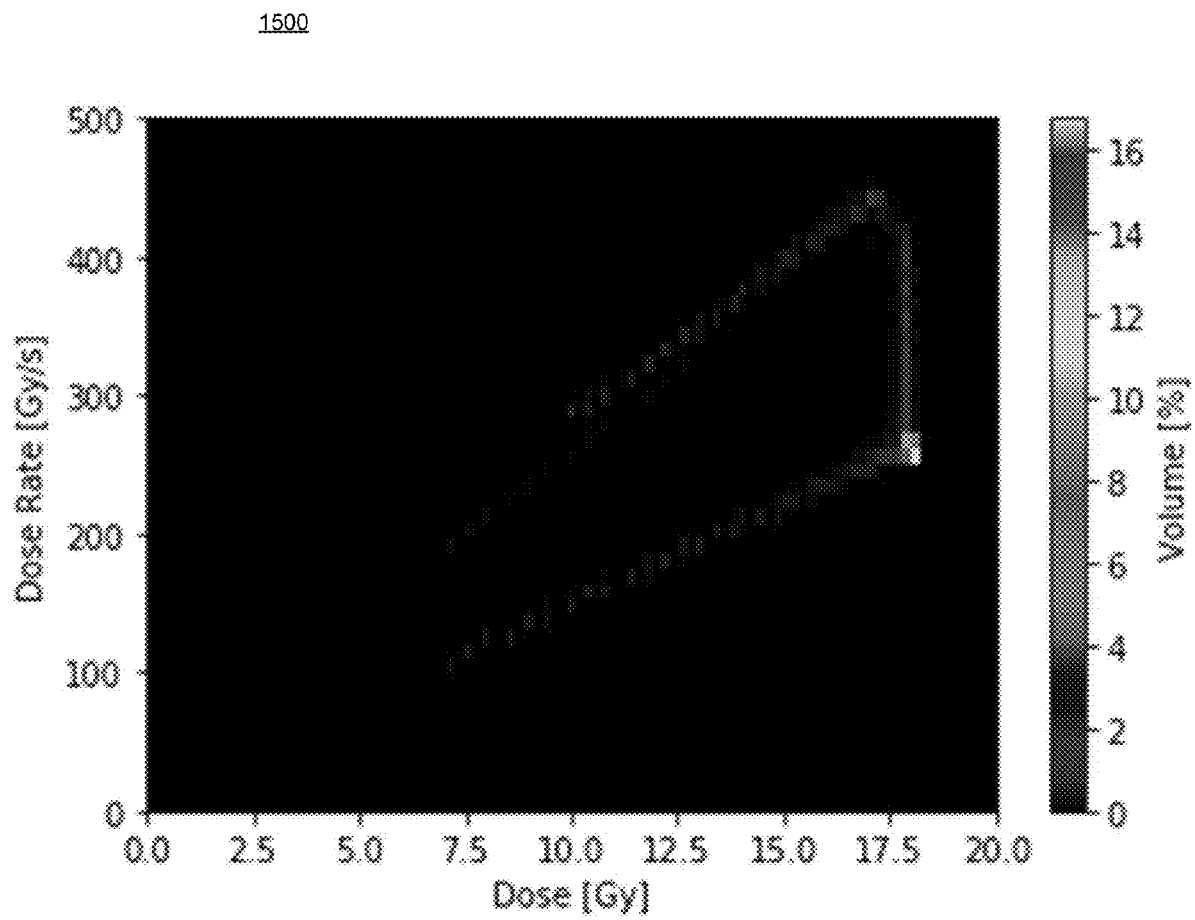
Figure 16:
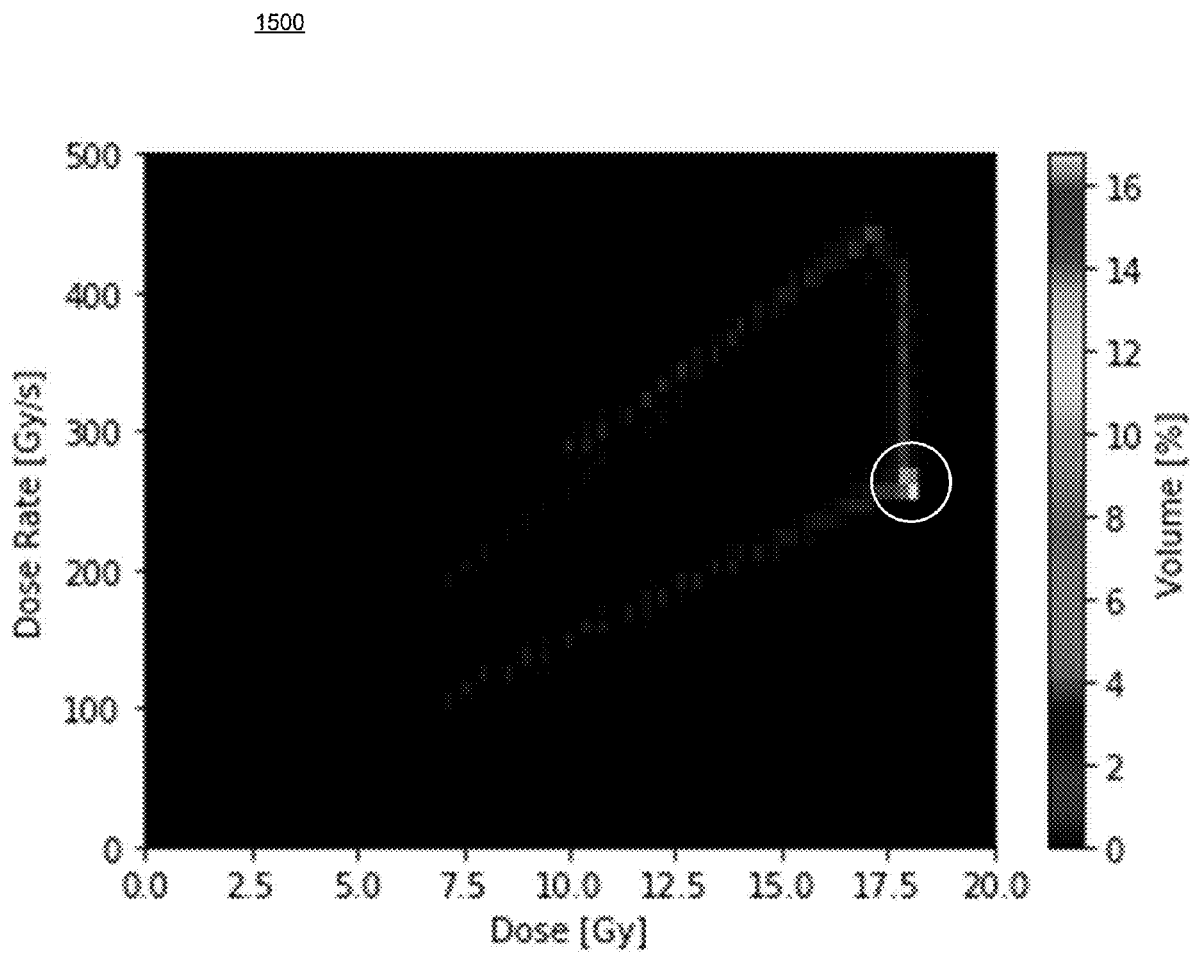
Figure 17:
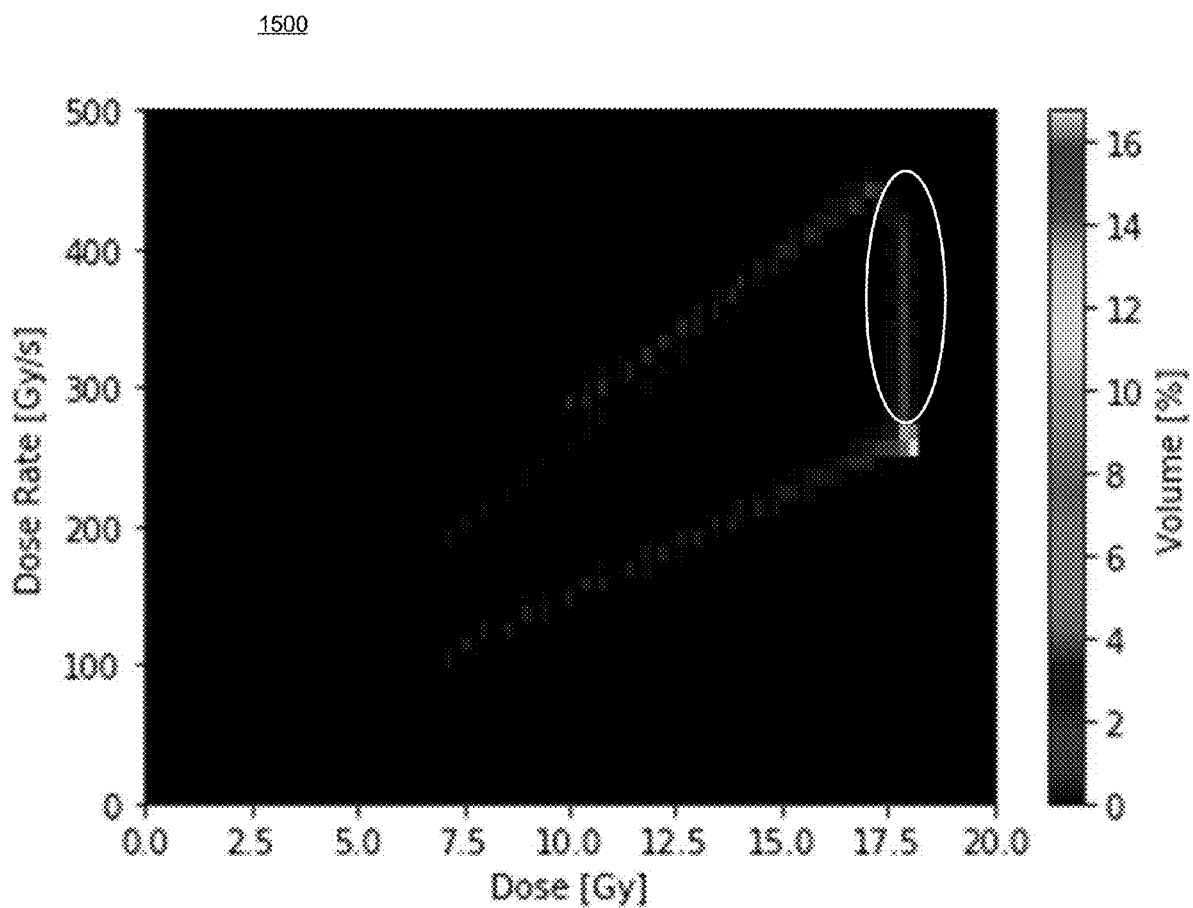
Figure 18:
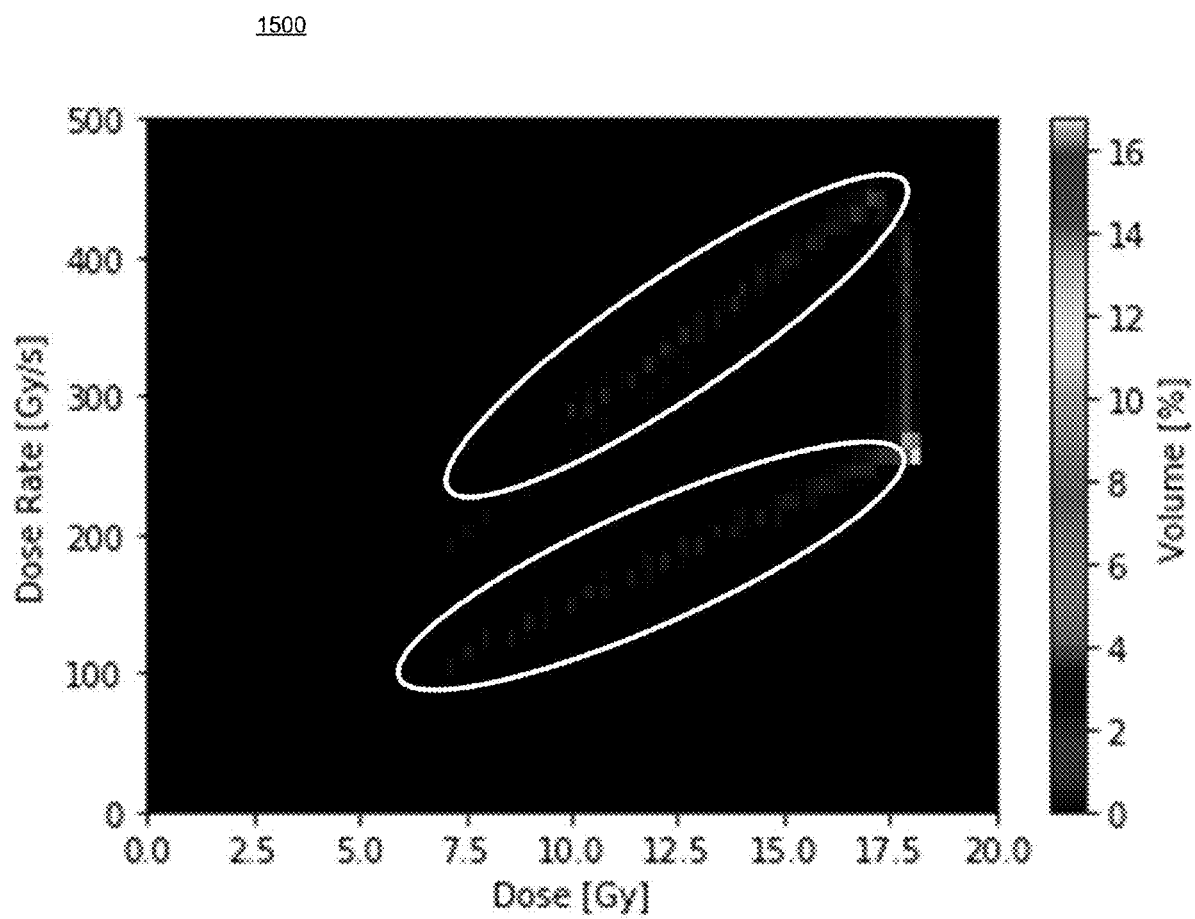

In the example of FIG. 15, the GUI 1500 includes a two-dimensional rendering of levels (ranges or bins) of dose rate on one axis and levels (ranges or bins) of dose on another axis. A measure (percentage) of the volume that receives a given combination of dose and dose rate is projected into the rendering. In the example of FIG. 15, approximately nine percent of the volume receives a dose of at least approximately 17.5 Gy at a dose rate of approximately 250 Gy per second. The projection of the volume can be color-coded to indicate the measure of the volume that receives a given dose and dose rate. In the example of FIG. 15, a color key is included in the GUI 1500 to associate colors in the rendering with the different measures of the volume. The color or colors of the projection of the volume can be compared to the colors in the key to determine the level of dose/dose rate for each of the smaller areas.

The GUI 1500 allows gross quantitative properties to be readily visualized and identified. For instance, as shown by the circled areas in FIGS. 16, 17, and 18, a peak of 18 Gy and 260 Gy per second, in-field dose rate gradients, and field edges, respectively, are readily visualized.

Figure 19:
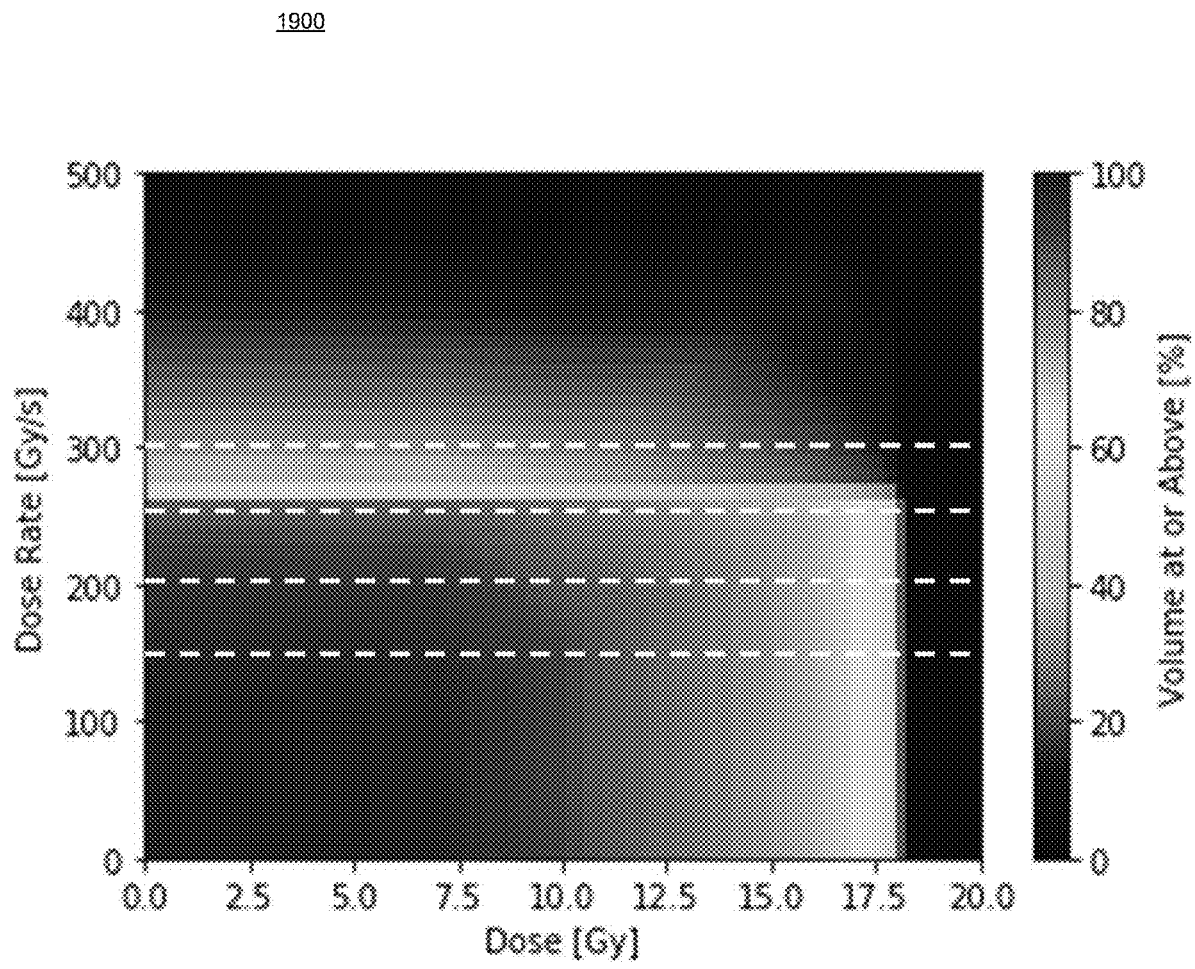

In the example of FIG. 19, the GUI 1900 includes a two-dimensional rendering of levels (ranges or bins) of dose rate on one axis and levels (ranges or bins) of dose on another axis. In this example, for each point in the rendering, the measure (e.g., percentage) of the volume at or above a dose level and dose rate is represented as a color. In the example of FIG. 19, a color key is included in the GUI 1900 to associate colors in the rendering with the different measures of the volume. Also, in this example, horizontal slices (indicated by the dashed lines in FIG. 19) represent the DVH of regions of the volume above a given dose rate.

Figure 20:
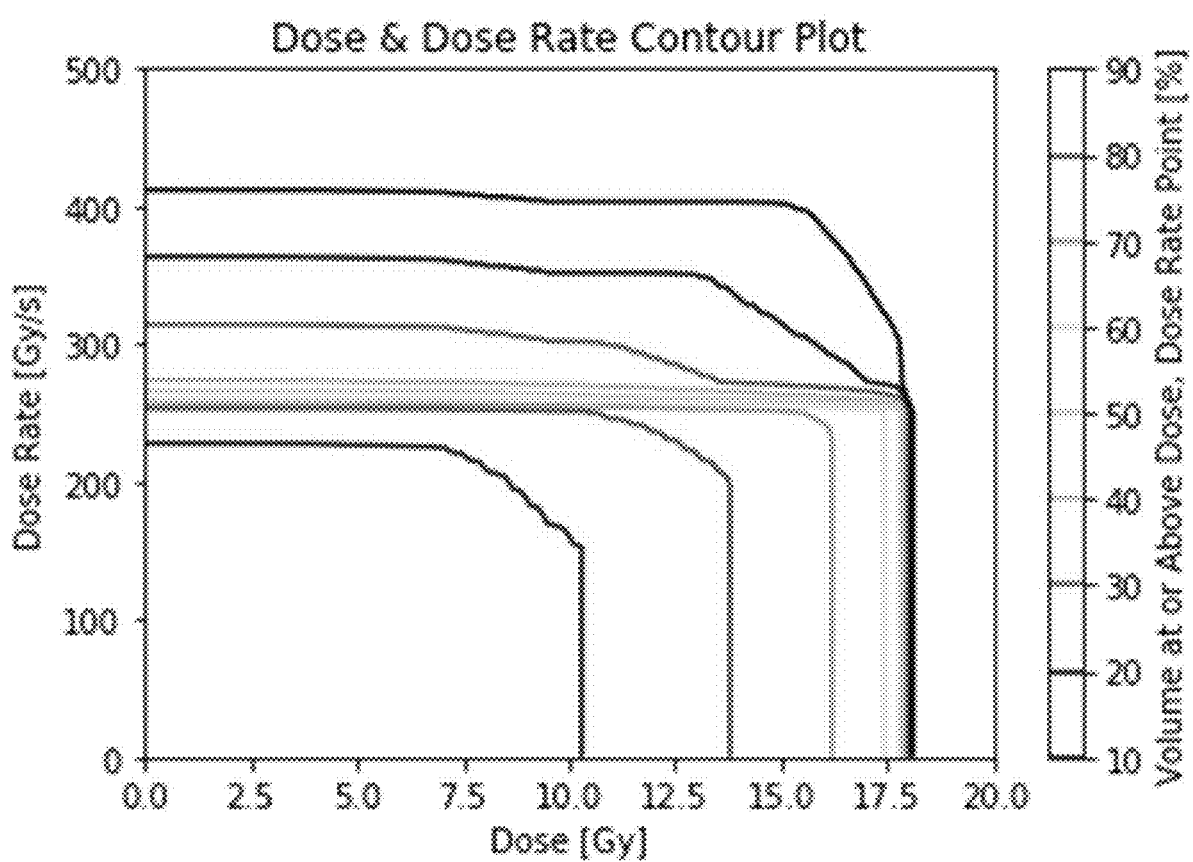
Figure 21:
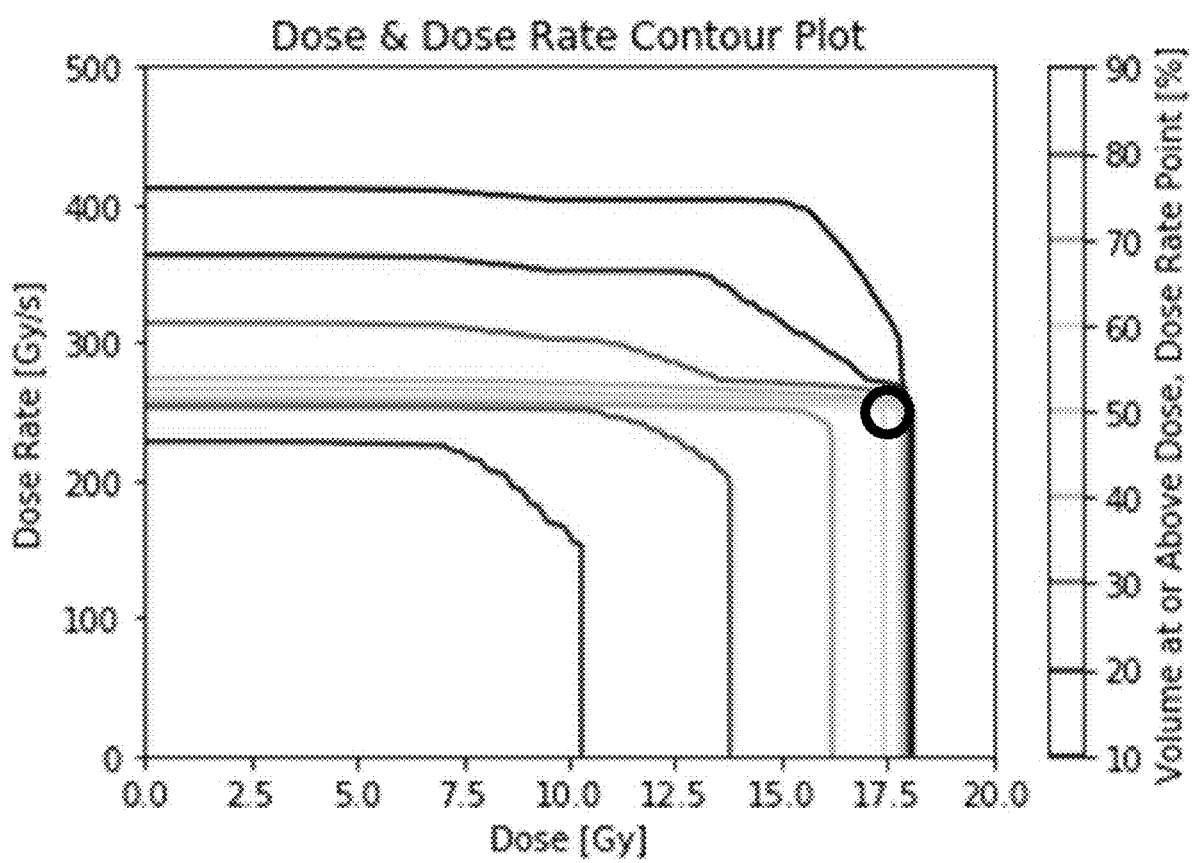

In the example of FIG. 20, the GUI 2000 includes a two-dimensional rendering of levels (ranges or bins) of dose rate on one axis and levels (ranges or bins) of dose on another axis. In this example, each line in the rendering represents the measure (e.g., percentage) of the volume at or above a given dose level and dose rate. In the example of FIG. 20, each line is a different color, and a color key is included in the GUI 2000 to associate the colors of the lines in the rendering with the different measures of the volume. For instance, in the example of FIG. 21, approximately 60 percent of the volume is receiving at least 17.5 Gy at a dose rate of at least 250 Gy per second.

Figure 22:
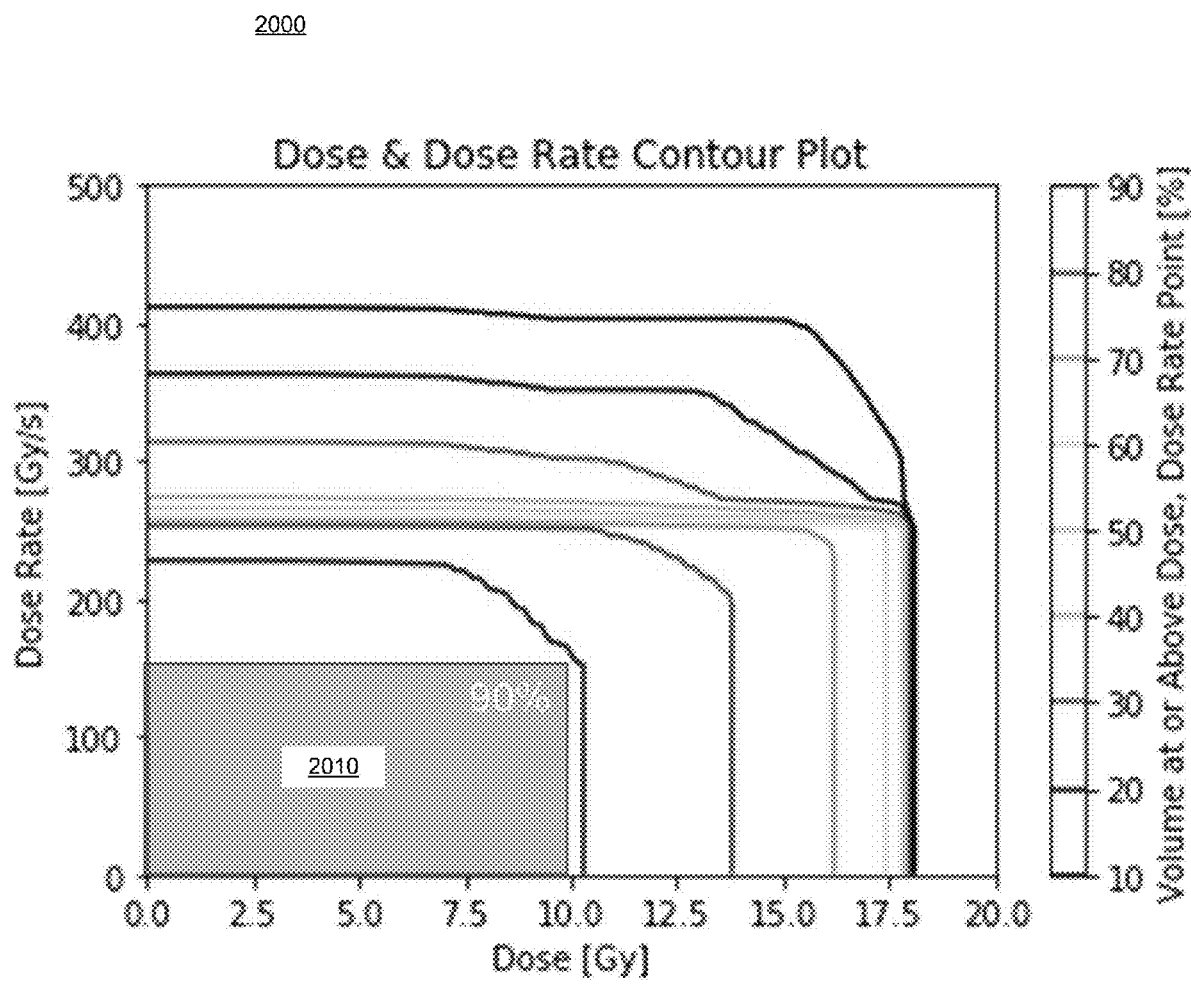

In the example of FIG. 22, the GUI 2000 also includes a region 2010 representing a prescription dose and dose rate. In this example, the prescription is for at least 150 Gy per second to 90 percent of the volume receiving more than 10 Gy. In this example, the prescription is met because the region 2010 is surrounded by the line corresponding to 90 percent of the volume.

Figure 23:
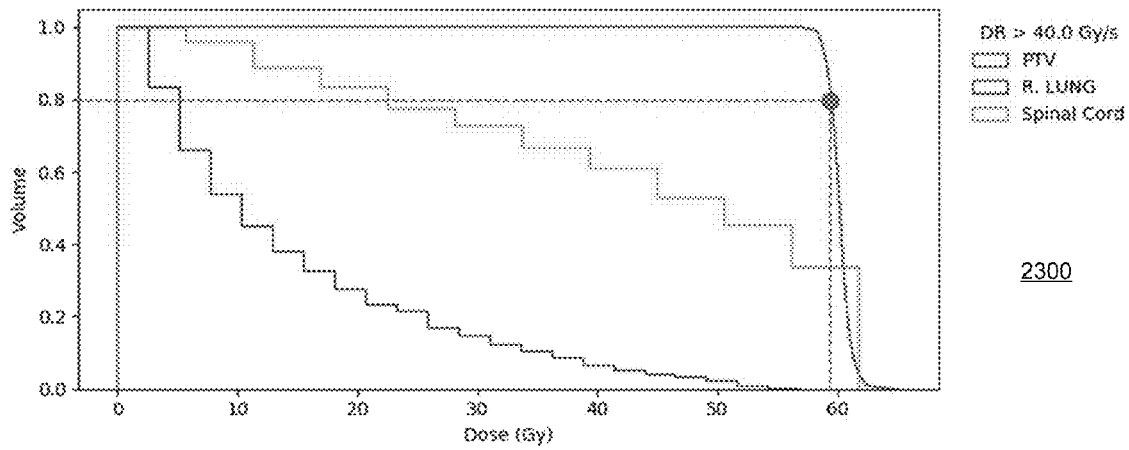

In the example of FIG. 23, the GUI 2300 includes, for a given dose rate (e.g., at least 40 Gy per second), a two-dimensional rendering of levels (ranges or bins) of dose rate on one axis and a measure (fraction) of volume that receives a given dose on another axis. In this example, each line in the rendering represents a different sub-volume (e.g., a planning target volume (PTV), the right lung, and the spinal cord). In the example of FIG. 23, each line is a different color, and a color key is included in the GUI 2300 to associate the colors of the lines in the rendering with the associated sub-volume. In the example, 80 percent of the PTV receives a dose above 60 Gy and a dose rate of 40 Gy per second.

Figure 24:
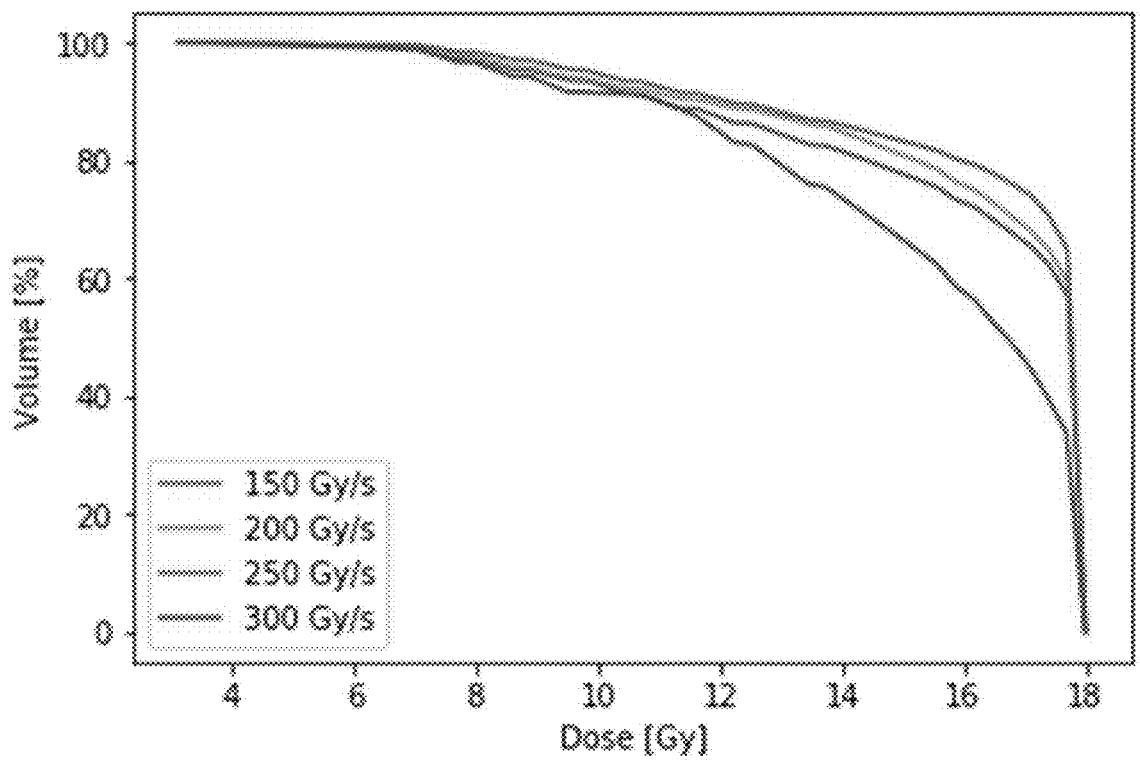

In the example of FIG. 24, the GUI 2400 includes a two-dimensional rendering of levels (ranges or bins) of dose rate on one axis and a measure (percentage) of volume that receives a given dose on another axis. The GUI 2400 represents a plot of the DVH for a region at or above a certain dose rate. In this example, each line in the rendering represents a different dose rate. In the example of FIG. 24, each line is a different color, and a color key is included in the GUI 2400 to associate the colors of the lines in the rendering with the different dose rate.

Figure 25:
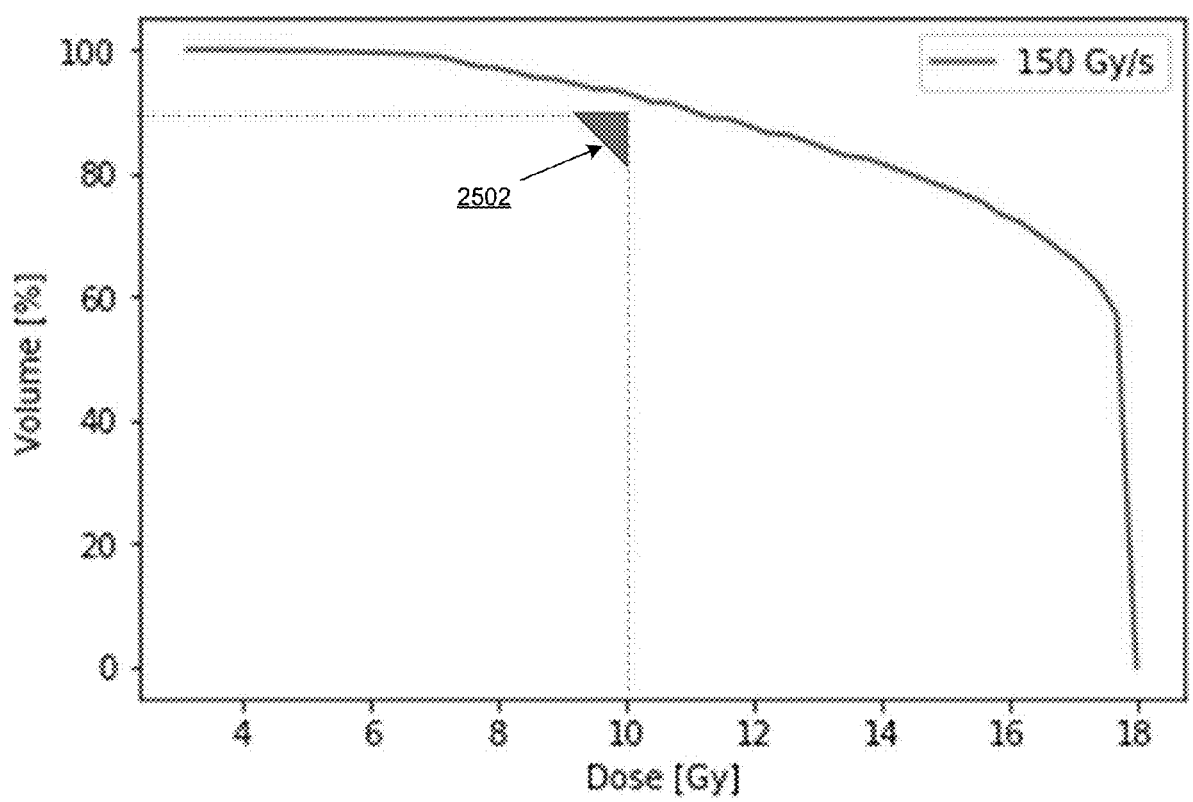

In the example of FIG. 25, the GUI 2500 includes, for a given dose rate (e.g., 150 Gy per second), a two-dimensional rendering of levels (ranges or bins) of dose rate on one axis and a measure (percentage) of volume that receives a given dose on another axis. The GUI 2500 represents a visualization (plot) of the DVH for a region at or above the given dose rate. In the example of FIG. 25, the GUI 2500 also includes a region 2502 representing a prescription dose and dose rate. In this example, the prescription is for at least 150 Gy per second to 90 percent of the volume receiving more than 10 Gy.

Figure 26:
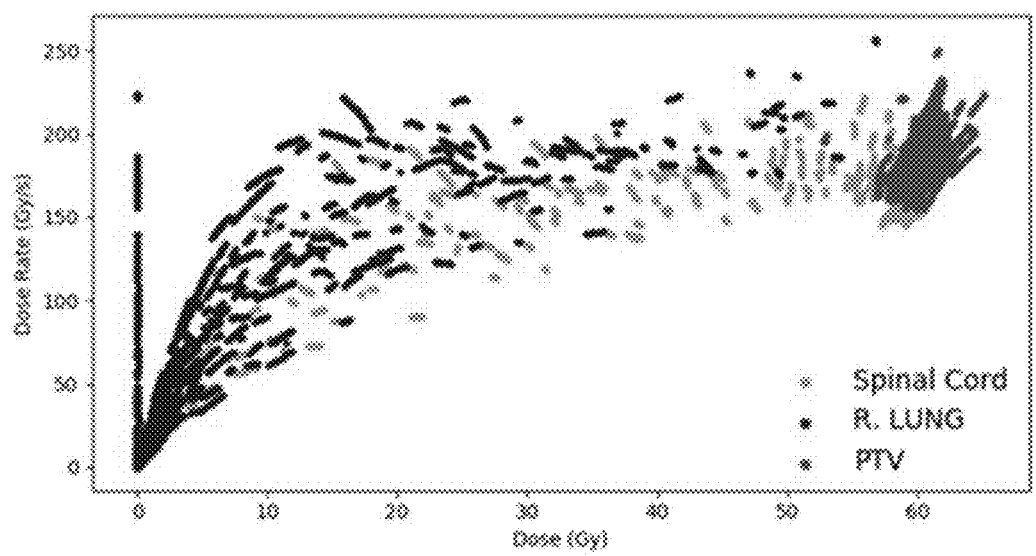

In the example of FIG. 26, the GUI 2600 includes a rendering of a scatter plot of levels (ranges or bins) of dose rate on one axis and levels (ranges or bins) of dose on another axis, showing dose and dose rate distributions for different sub-volumes (e.g., spinal cord, right lung, and PTV). In this example, each sub-volume is represented as a different color, and a color key is included in the GUI 2600 to associate the colors in the rendering with the different sub-volumes.

Figure 27:
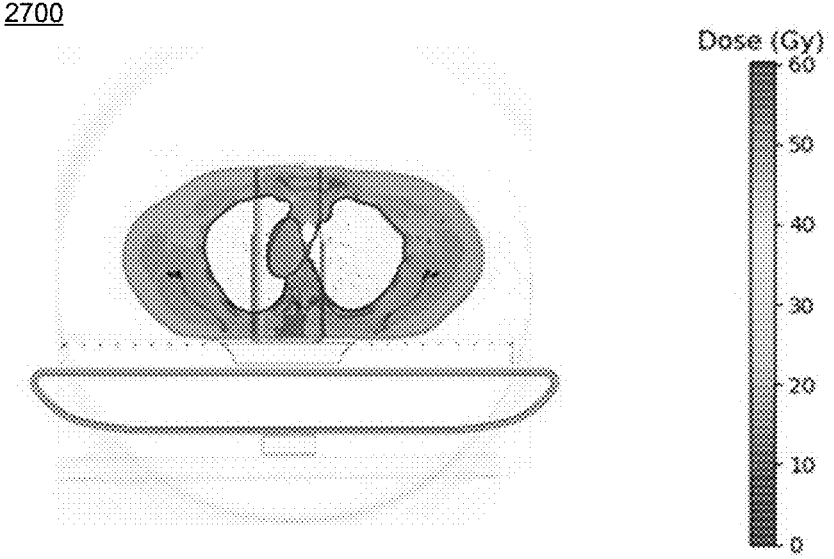
Figure 28:
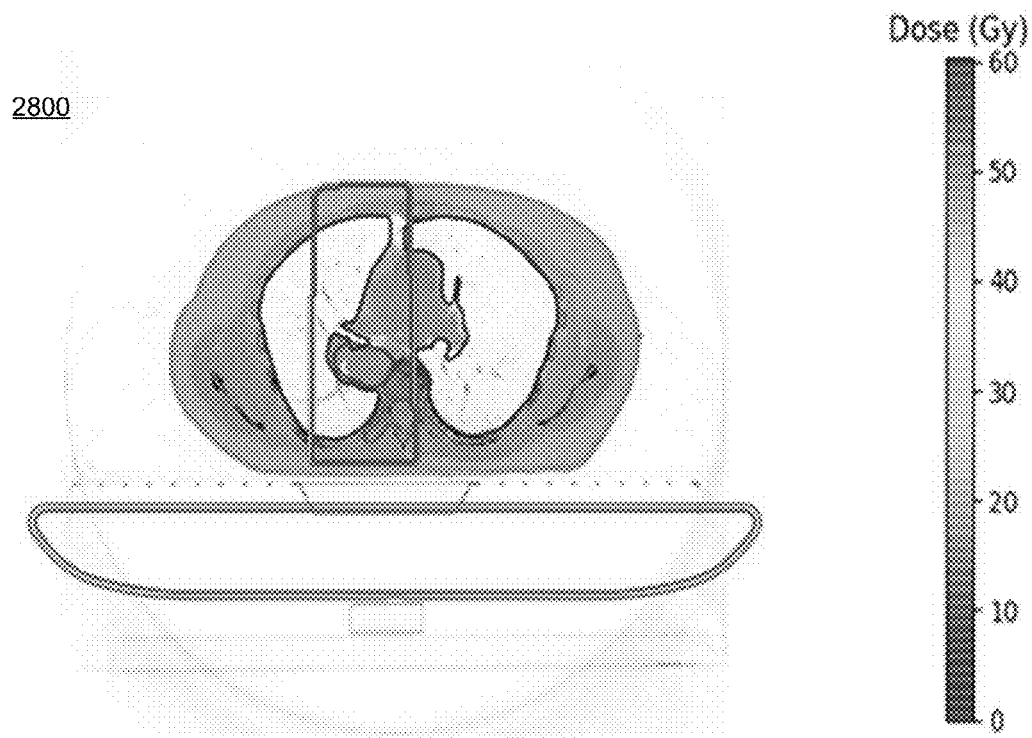

In the examples of FIGS. 27 and 28, the GUIs 2700 and 2800 include a rendering of a volume (e.g., a CT image). In these examples, different colors of contour lines are used to outline portions (e.g., voxels) in the volume that have a dose and dose rate above a certain threshold, below a certain threshold, or within a certain range. A color key is included in the GUIs 2700 and 2800 to associate the colors in the rendering with, for example, level of dose. In the example of FIG. 27, the dose distribution is shown in the delineated rectangular region only for the sub-volumes (voxels) with a dose rate between 40 and 120 Gy per second. In the example of FIG. 28, the delineated rectangular region encompasses voxels that have a dose above 10 Gy and a dose rate above 10 Gy per second.

Figure 29A:
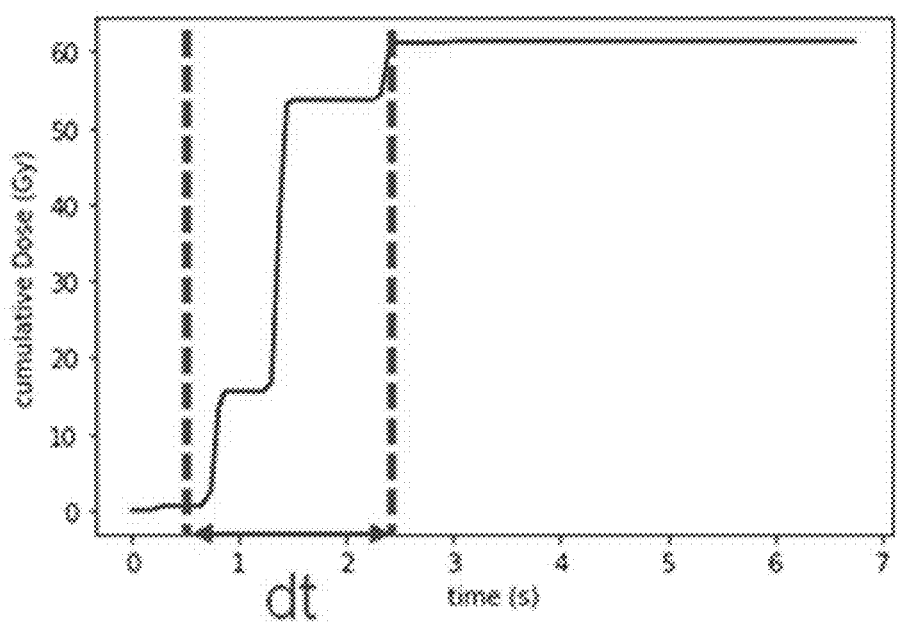

In the example of FIG. 29A, the GUI 2900 includes a rendering of cumulative dose versus time. The GUI 2900 is useful for determining a time interval (dt) needed to deliver a given level of dose (e.g., 90 percent).

Figure 29B:
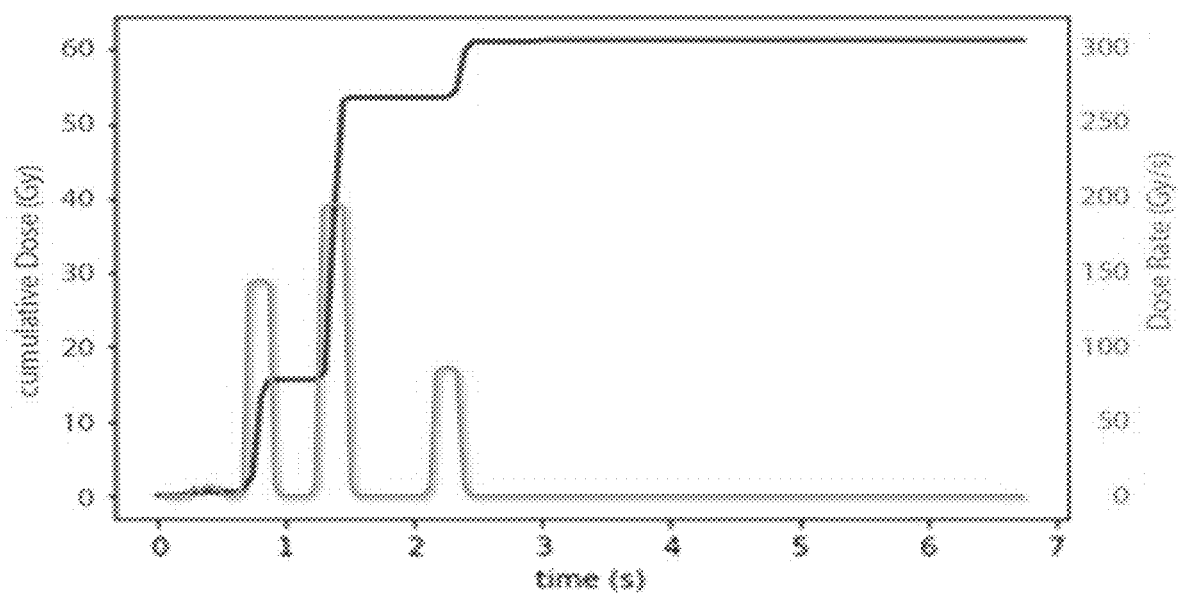

FIG. 29B illustrates an example of a GUI 2910 in which more than one dose rate is specified per voxel. When a particular dose or dose rate range is specified, the corresponding dose is displayed. In the example of FIG. 29B, the lower line in the figure (which can be displayed using a first color) represents the dose rate as a function of time, and the upper line in the figure (which can be displayed as a second, different color) represents the cumulative dose as a function of time. The slope of the upper line is the dose rate as a function of time. For the voxel that is illustrated, the GUI 2910 provides a visualization of dose, mean dose rate, and the dose that would be delivered for a dose rate or range of dose rates. In the example, the GUI 2910 shows that the dose is 60 Gy, the mean dose rate is about 40 Gy per second, and a dose of about 40 Gy is delivered with a dose rate in the range from 150 to 200 Gy per second.

Figure 30A:
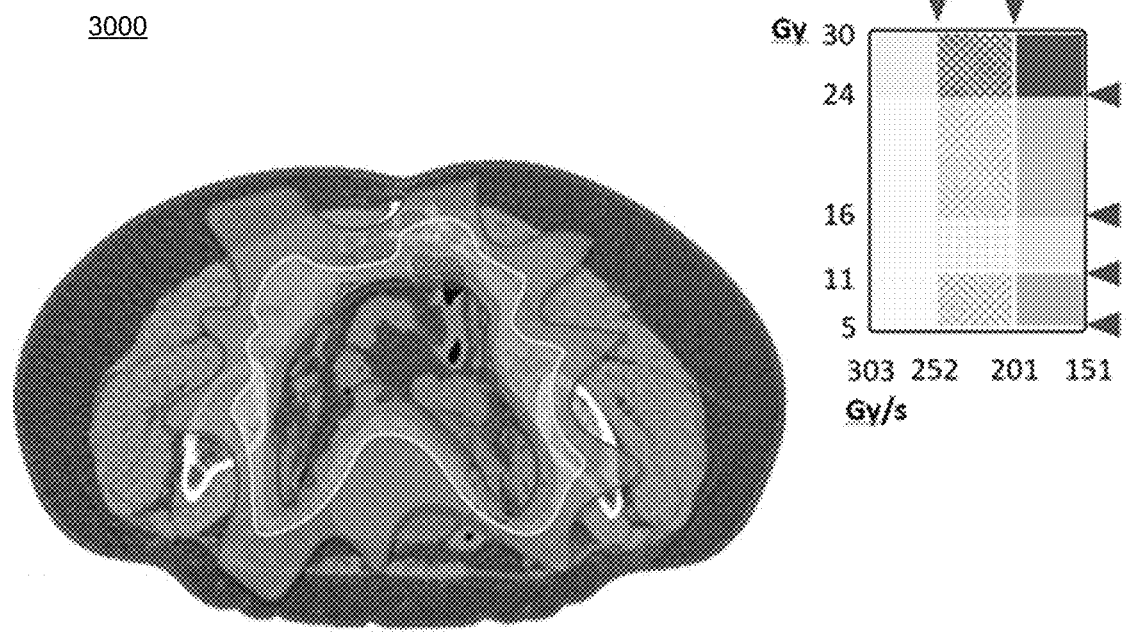

In the example of FIG. 30A, the GUI 3000 includes a rendering of an overlay of isodose contour lines on a dose rate distribution in a volume (e.g., a CT image). In the example of FIG. 30A, different colors are used to indicate different dose levels and different dose rates. A color key is included in the GUI 3000 to associate the colors in the rendering with dose level and dose rate. The rendering can be manipulated using the key, by using the pointers shown in the figure to select different levels of dose and different dose rates to be rendered in the GUI 3000. For example, one color can be used to represent a dose in the range of 5-11 Gy, and different shades of that color can be used to represent different ranges of dose rate corresponding to that range of doses (e.g., 151-201, 201-252, and 252-303 Gy per second). A user can interactively change the positions of the pointers on either or both the vertical and horizontal axes. By changing the positions of those pointers, the respective ranges of dose and dose rate associated with a particular color or shading are also changed, and the isodose contour lines in the GUI 3000 would also be changed accordingly.

Figure 30B:
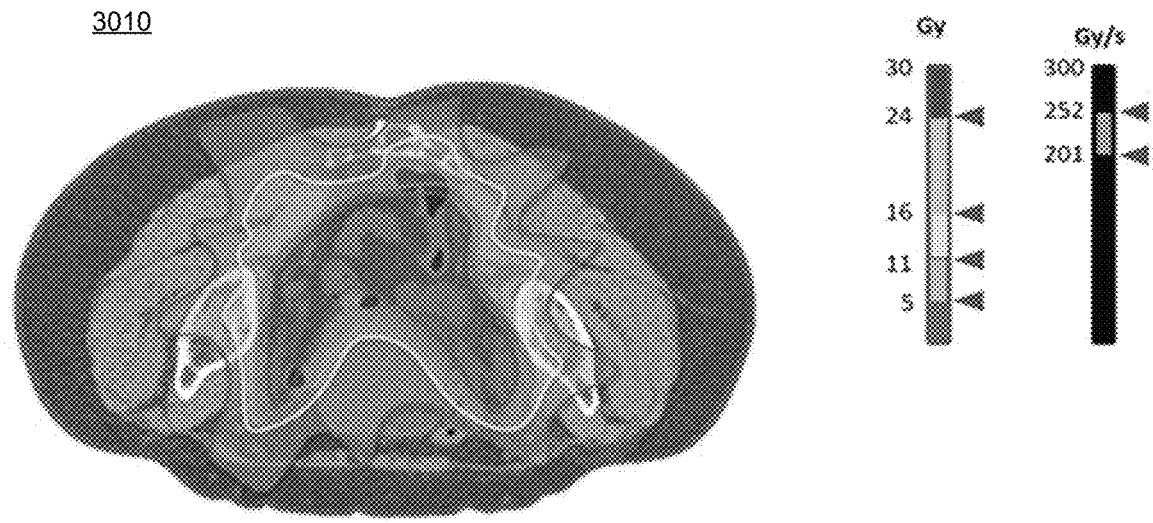

FIG. 30B illustrates an example of a GUI 3010 in which a dose corresponding to a particular range of dose rates is rendered on top of a CT image (e.g., the CT image also shown in FIG. 30A). In this example, a dose rate range constraint is applied individually for each voxel, and the corresponding fraction of dose is visualized. Alternatively, the dose rate distribution subject to a constraint of the accumulated dose in each voxel can be visualized; for example, a GUI may show, in each voxel, the dose rate at which X percent of the dose at each voxel has been accumulated. A user can select the dose percentage that is used to select the dose rate displayed per voxel. Similar to that described above, a user can also interactively select and adjust the positions of pointers to associate a color with a dose range. In this example, the user can also adjust the positions of pointers to select a dose rate range. Only the dose that would be delivered with the selected dose rate is rendered in the GUI 3010. The example of FIG. 30B shows isodose contour lines for doses that would be delivered for a dose rate range of 201-252 Gy per second.

Figure 31:
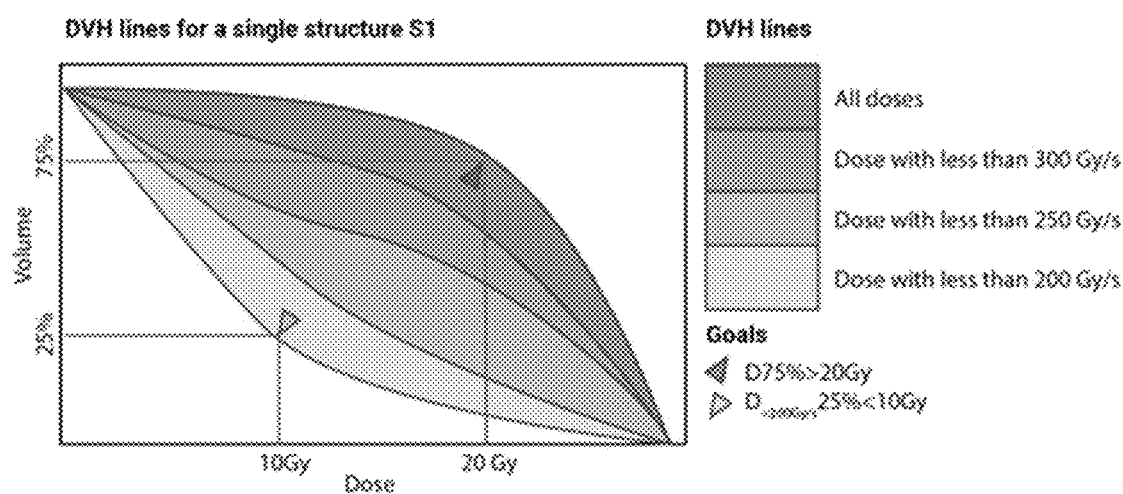

In the example of FIG. 31, the GUI 3100 includes, for a given volume or sub-volume (e.g., structure "S1"), a two-dimensional rendering of levels (ranges or bins) of dose rate on one axis of a plot and a measure (percentage) of volume that receives a given dose on another axis of the plot. The lines in the plot delineate different regions of the visualization. Those lines bound regions representing different DVHs corresponding to different dose rates. In this example, each region is represented by a different level of shading, and a key is included in the GUI 3100 to associate the level of shading in the visualization with dose level and dose rate. Also, in this example, different pointers are included in the rendering to indicate different goals (e.g., prescription dose and dose rate).

Figure 32:
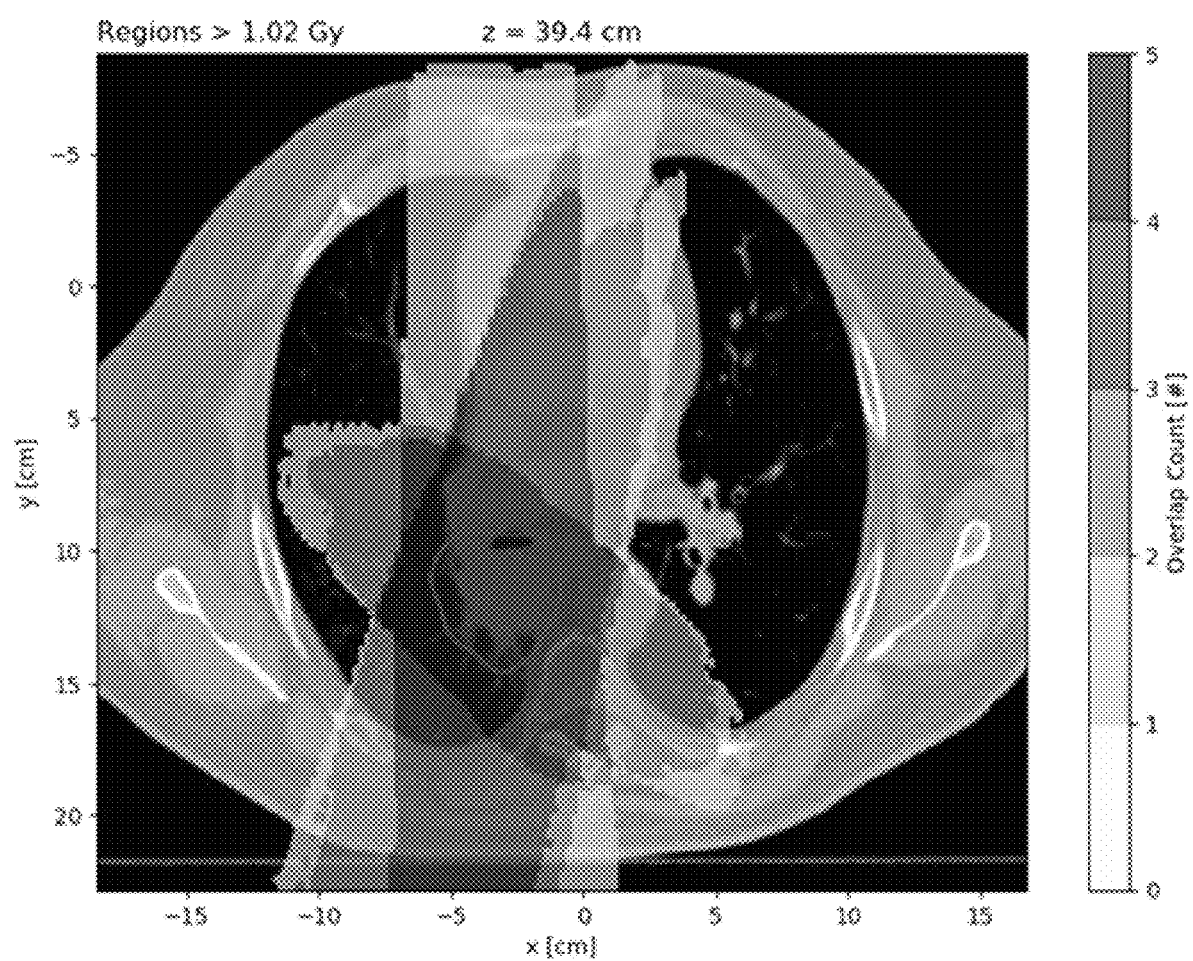

In the example of FIG. 32, the GUI 3200 includes a rendering of regions where beams overlap in three dimensions. The number of times a voxel is traversed by a beam is color-coded. The GUI 3200 includes x and y coordinates in the plane of the volume shown in the visualization, and also includes a z coordinate that indicates the depth of the plane in the volume. A particular target in the volume is outlined in the example of FIG. 32. In this example, five beams are shown, and a key is included in the GUI 3200 to associate a color of a voxel to the number of beams that reach that voxel.

Figure 33:
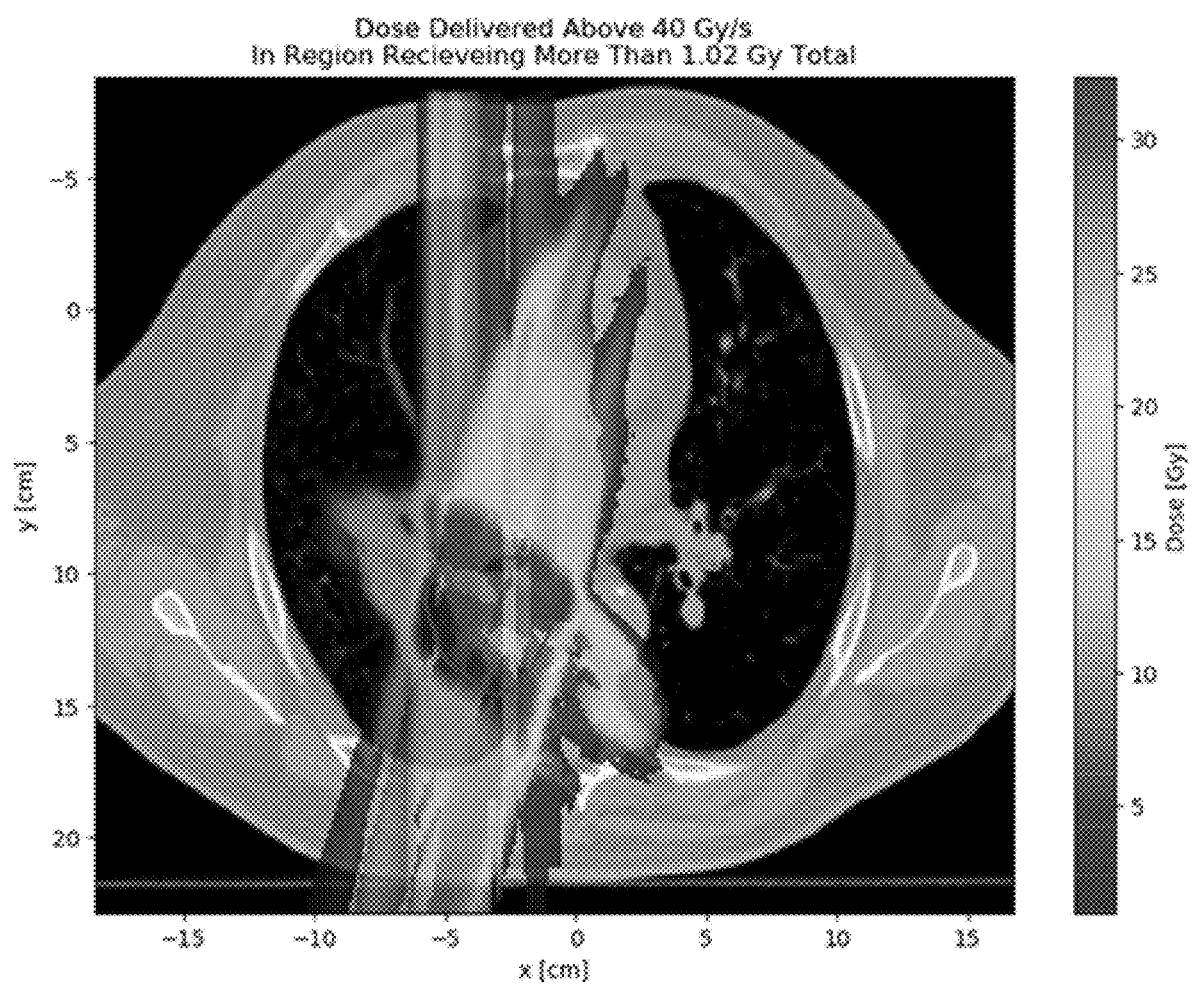

In the example of FIG. 33, the GUI 3300 includes a rendering of cumulative dose delivered above a certain dose rate threshold (e.g., above 40 Gy per second). In the example of FIG. 33, different colors are used to indicate different cumulative doses. A color key is included in the GUI 3300 to associate the colors in the rendering with dose level and dose rate. A particular target in the volume is outlined in the example of FIG. 33.

Figure 34:
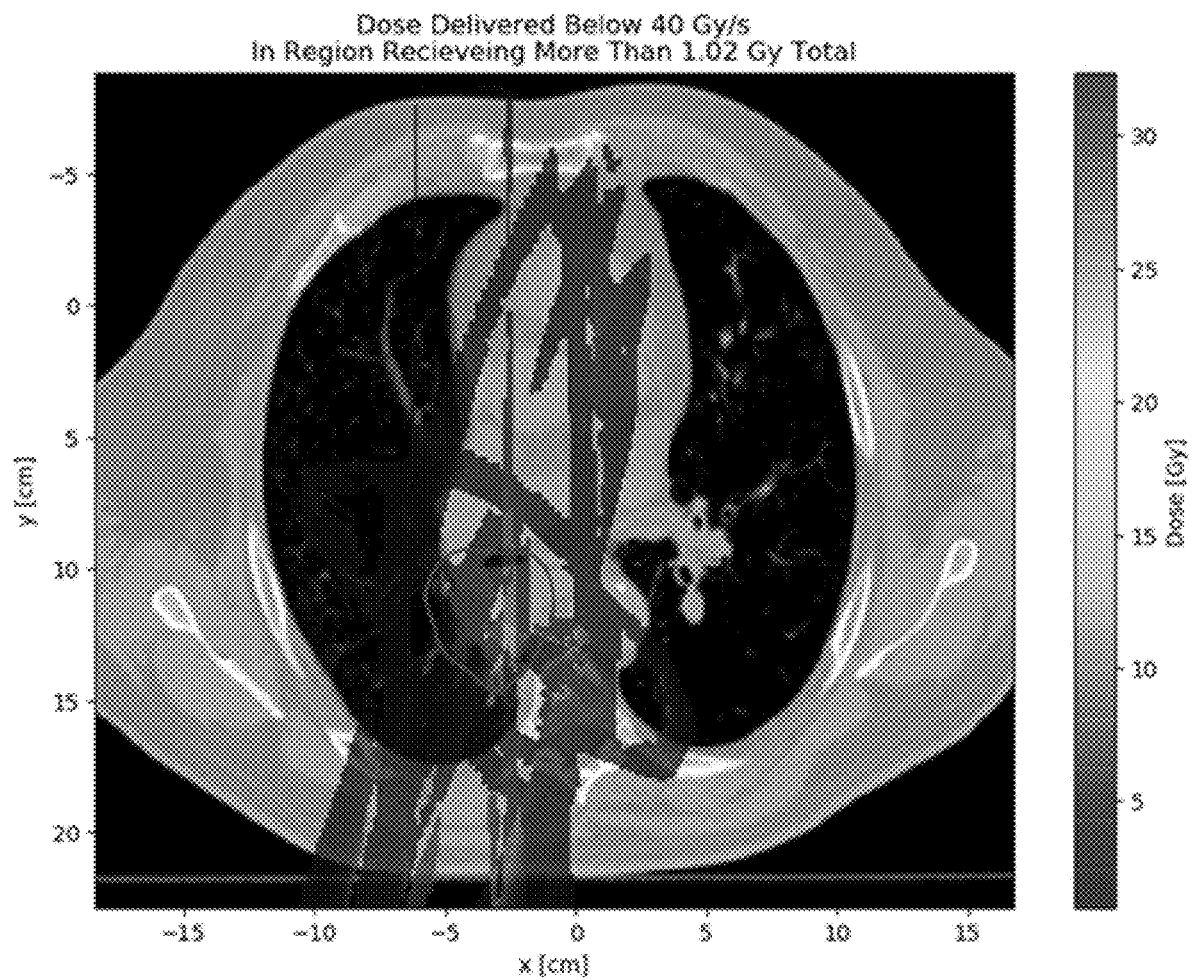

In the example of FIG. 34, the GUI 3400 includes a rendering of cumulative dose delivered below a certain dose rate threshold (e.g., below 40 Gy per second). In the example of FIG. 34, different colors are used to indicate different cumulative doses. A color key is included in the GUI 3400 to associate the colors in the rendering with dose level and dose rate. A particular target in the volume is outlined in the example of FIG. 34.

Figure 35:
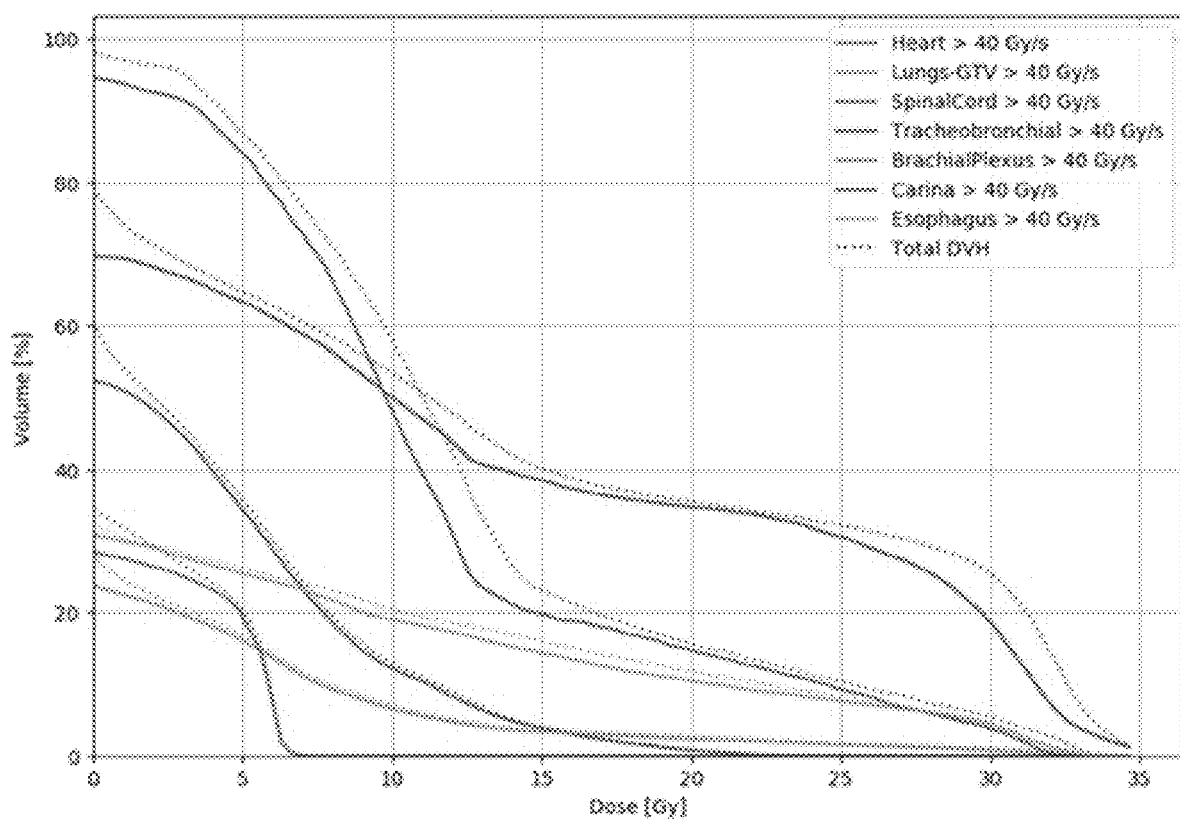

In the example of FIG. 35, the GUI 3500 includes a rendering of a DVH of dose delivered above a certain dose rate threshold (e.g., above 40 Gy per second). In this example, dotted lines represent the total DVH, and solid lines represent the DVH above a certain dose rate threshold (e.g., above 40 Gy per second). The difference between each pair of solid and dotted lines indicate the portion of the organ at risk volume that was not delivered a sufficiently high dose rate. In the example of FIG. 35, different colors are used to indicate different organs or structures. A color key is included in the GUI 3500 to associate the colors in the rendering with the different organs or structures.

In summary, embodiments according to the invention improve radiation treatment planning and the treatment itself by expanding FLASH RT to a wider variety of treatment platforms and target sites. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to those benefits, a GUI facilitates treatment planning by allowing a planner to readily visualize key elements of a proposed treatment plan (e.g., the dose rate per sub-volume), to readily visualize the effects on those elements of changes to the proposed plan, and to readily visualize a comparison between different plans.

In addition to radiation therapy techniques in which the intensity of the particle beam is either constant or modulated across the field of delivery, such as IMRT and IMPT, embodiments according to the invention can be used in spatially fractionated radiation therapy including high-dose spatially fractionated grid radiation therapy, minibeam radiation therapy, and microbeam radiation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
a processor;
a display device coupled to the processor; and
a memory coupled to the processor, the memory storing instructions that, when executed by the processor, cause the computer system to
access information including calculated doses and calculated dose rates for a plurality of sub-volumes in a volume in a treatment target,
access information including values of a measure of the plurality of sub-volumes as a function of the calculated doses and the calculated dose rates, and
display, via the display device, a graphical user interface (GUI) including, in a single rendering, a representation of the calculated doses, the calculated dose rates, and the values of the measure.

2. The computer system of claim 1, wherein the single rendering comprises a visualization of a dose-volume histogram as a first dimension of the GUI, a visualization of a dose rate-volume histogram as a second dimension of the GUI, and a visualization of the values of the measure as a third dimension of the GUI.

3. The computer system of claim 1, wherein the single rendering comprises a visualization of a calculated dose per sub-volume of the plurality of sub-volumes.

4. The computer system of claim 1, wherein the single rendering comprises a visualization of a calculated dose rate per sub-volume of the plurality of sub-volumes.

5. The computer system of claim 1, wherein the single rendering comprises a visualization of a value of the measure per sub-volume of the plurality of sub-volumes.

6. A computer system, comprising:
a processor;
a display device coupled to the processor; and
a memory coupled to the processor, the memory storing instructions that, when executed by the processor, cause the computer system to
access information including calculated doses and calculated dose rates for a plurality of sub-volumes in a volume in a treatment target,
access information including values of a measure of the plurality of sub-volumes as a function of the calculated doses and the calculated dose rates, and
display, via the display device, a graphical user interface (GUI) including a rendering that is based on the calculated doses, the calculated dose rates, and the values of the measure, wherein
the rendering includes a visualization of a prescription dose and a prescription dose rate.

7. The computer system of claim 1, wherein the GUI further comprises a visualization of normal tissue complication probability per sub-volume of the plurality of sub-volumes.

8. The computer system of claim 1, wherein the GUI further comprises a visualization of tumor control probability per sub-volume of the plurality of sub-volumes.

9. The computer system of claim 1, wherein the memory stores instructions that, when executed by the processor, cause the computer system to
associate attribute values to elements of the single rendering corresponding to the calculated doses, the calculated dose rates, and the values of the measure; and
display the elements according to the attribute values.

10. The computer system of claim 9, wherein the attribute values are values of attributes including at least one of color, pattern, gray-scale, alphanumeric text, or brightness.

11. The computer system of claim 1, wherein the single rendering includes a visualization of a prescription dose and a prescription dose rate.

12. The computer system of claim 1, wherein the single rendering further comprises isodose contour lines and isodose rate contour lines.

13. A computer system, comprising:
a processor;
a display device coupled to the processor; and
a memory coupled to the processor, the memory storing instructions that, when executed by the processor, cause the computer system to
access information including calculated doses and calculated dose rates for a plurality of sub-volumes in a volume in a treatment target,
access information including values of a measure of the plurality of sub-volumes as a function of the calculated doses and the calculated dose rates, and
display, via the display device, a graphical user interface (GUI) including a rendering that is based on the calculated doses, the calculated dose rates, and the values of the measure, wherein
the rendering includes isodose contour lines and isodose rate contour lines.

14. A non-transitory computer-readable storage medium having computer-executable instructions for causing a computer system to perform a method used for planning radiation treatment, the method comprising:
accessing a radiation treatment plan including a number of beams to be directed at and into a volume in a treatment target, directions of the beams, and a range of dose rates for each of the beams, wherein the volume includes a plurality of sub-volumes;
calculating a dose per sub-volume of the plurality of sub-volumes using the number and directions of the beams and the range of dose rates;
calculating a dose rate per sub-volume of the plurality of sub-volumes using the number and directions of the beams and the range of dose rates;
determining, for different levels of dose and different levels of dose rate, a value of a measure of the sub-volumes that are calculated to receive at least a respective level of dose and at least a respective level of dose rate; and
displaying, on a display device of the computer system, a graphical user interface (GUI) including a rendering of a representation of the calculated dose per sub-volume of the plurality of sub-volumes, the calculated dose rate per sub-volume of the plurality of sub-volumes, and the value of the measure of the sub-volumes that are calculated to receive at least the respective level of dose and at least the respective level of dose rate.

15. The non-transitory computer-readable storage medium of claim 14, wherein the rendering comprises a visualization of a dose-volume histogram as a first dimension of the GUI, a visualization of a dose rate-volume histogram as a second dimension of the GUI, and a visualization of the value of the measure as a third dimension of the GUI.

16. The non-transitory computer-readable storage medium of claim 14, wherein the rendering further comprises one or more of a visualization of a prescription dose and a prescription dose rate, a visualization of normal tissue complication probability per sub-volume of the plurality of sub-volumes, or a visualization of tumor control probability per sub-volume of the plurality of sub-volumes.

17. The non-transitory computer-readable storage medium of claim 14, wherein the method further comprises:
associating attribute values to elements of the rendering corresponding to the calculated doses, the calculated dose rates, and the value of the measure; and
displaying the elements according to the attribute values.

18. The non-transitory computer-readable storage medium of claim 14, wherein the rendering is a single rendering.

19. A non-transitory computer-readable storage medium having computer-executable instructions for causing a computer system to perform a method used for planning radiation treatment, the method comprising:
generating a dose-volume histogram (DVH) for a volume in a treatment target, wherein the DVH indicates a measure of the volume that receives a dose;
generating a dose rate-volume histogram (DRVH) for the volume in the treatment target, wherein the DRVH indicates a measure of the volume that receives a dose rate; and
displaying, on a display device of the computer system, a graphical user interface (GUI) including a combined rendering of the DVH and the DRVH, wherein the combined rendering visualizes a measure of the volume that is calculated to receive a given dose as a function of dose rate and also a measure of the volume that is calculated to receive a given dose rate as a function of dose.

20. The non-transitory computer-readable storage medium of claim 19, wherein the GUI comprises a visualization of the DVH as a first dimension of the GUI, a visualization of the DRVH as a second dimension of the GUI, and a visualization of values of the measure as a third dimension of the GUI.

21. The non-transitory computer-readable storage medium of claim 19, wherein the combined rendering comprises one or more of a visualization of calculated dose per sub-volume of a plurality of sub-volumes of the volume, a calculated dose rate per sub-volume of the plurality of sub-volumes, or a visualization of a value of the measure per sub-volume of the plurality of sub-volumes.

22. The non-transitory computer-readable storage medium of claim 19, wherein the combined rendering further comprises one or more of a visualization of a prescription dose and a prescription dose rate, a visualization of normal tissue complication probability per sub-volume of a plurality of sub-volumes of the volume, or a visualization of tumor control probability per sub-volume of the plurality of sub-volumes.

* * * * *